(12) United States Patent
Scott et al.

(10) Patent No.: US 6,509,369 B2
(45) Date of Patent: Jan. 21, 2003

(54) ANTI-INFLAMMATORY COMPOUNDS

(75) Inventors: Malcolm K. Scott, Lansdale, PA (US);
Pauline J. Sanfilippo, Chester Springs, PA (US); Louis J. Fitzpatrick, III, Souderton, PA (US); Richard Cordova, Whitehall, PA (US); Kevin Pan, Wayne, PA (US); Joseph Meschino, Avalon, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/041,423

(22) Filed: Jan. 8, 2002

(65) Prior Publication Data

US 2002/0103217 A1 Aug. 1, 2002

Related U.S. Application Data

(62) Division of application No. 09/221,254, filed on Dec. 28, 1998, now Pat. No. 6,372,779.
(60) Provisional application No. 60/068,928, filed on Dec. 29, 1997.

(51) Int. Cl.[7] ............... A61K 31/381; A61K 31/165; C07D 333/24; C07D 333/60; C07D 317/48; A61P 29/00
(52) U.S. Cl. ............... 514/438; 514/352; 514/415; 514/443; 514/447; 514/466; 514/448; 514/338; 514/617; 514/630; 546/309; 548/483; 548/492; 549/57; 549/64; 549/72; 549/77; 549/441; 564/219; 564/182; 564/170
(58) Field of Search ............... 546/309; 548/483, 548/492; 549/57, 64, 72, 77, 441; 564/219, 182, 170; 514/352, 415, 438, 443, 447, 466, 630, 617, 448, 338

(56) References Cited

U.S. PATENT DOCUMENTS

| | | | |
|---|---|---|---|
| 4,822,780 A | 4/1989 | Tsuda et al. | |
| 5,736,578 A | * 4/1998 | Watson et al. | ............... 514/624 |
| 6,028,112 A | * 2/2000 | Leboulluec et al. | ........ 514/530 |

FOREIGN PATENT DOCUMENTS

| | | |
|---|---|---|
| FR | 2 354 997 | 5/1977 |
| WO | WO 95/11880 A1 | 5/1995 |

OTHER PUBLICATIONS

Benjamin Blank, et al., Synthesis and Antialdosterone Activity ofSubstituted 2,3,3–Triphenylpropylamines, Research and Development Division, Mar. 21, 1969, pp. 873–876, vol. 12, Smith Kline and French Laboratories, Philadelphia, Pennsylvania.

Gi Hyeon Baek, et al., Homovanillic Amide Derivatives as Capsaicin Analogs and Their Analgesic Activity, Arch. Pharm. Res., Jul. 16, 1997, pp. 659–661, vol. 20, No. 5, Bioorganic Division, Yusong, Taejon, Korea.

\* cited by examiner

*Primary Examiner*—Evelyn Mei Huang

(57) ABSTRACT

This invention relates to anti-inflammatory compounds, methods of making such compounds and methods of using such compounds having the following structure:

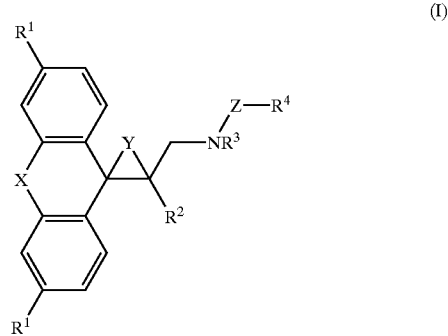

35 Claims, No Drawings

ANTI-INFLAMMATORY COMPOUNDS

This patent application is a divisional application of U.S. Ser. No. 09/221,254, filed Dec. 28, 1998, U.S. Pat. No. 6,372,779, which claims benefit of provisional application No. 60/068928, filed on Dec. 29, 1997, and hereby incorporates said patent application by reference herein.

BACKGROUND OF THE INVENTION

1. Filed of Invention

This invention relates to triphenylpropanamide compounds which are useful in treating inflammations but which do not demonstrate the side effects normally associated with other anti-inflammatory treatments such as glucocorticoids This invention also relates to methods for making and using the compounds of the invention.

2. Prior Art

Glucocorticoids are the only agents which reduce all the symptoms that are manifested in chronic adrenocortical disorder and hyperfunction, allergies, rheumatoid arthritis, lupus, inflammatory bowel disease, pneumonia bronchial asthma, hematological disorders, dermatitis and eczema. Glucocorticoids also reduce immunological response in organ transplants. The undesired side effects of these agents include hypertension, atherosclerosis, diabetes, hyperglycemia, bone Fining and electrolyte imbalance.

Mechanistically, glucocorticoids bind to the glucocorticoid receptor (GR) on the surface of leukocytes and the resulting glucocorticoid -GR complex migrates into Fe cell nucleus. There, the complex interacts with transcription factor AP-1 (activating protein-1), inhibiting its induction of genes that produce inflammatory cytokines and collagenase, thereby repressing the inflammatory process. However, the complex also activates GRE (glucocorticoid response element), a transcriptional activator of genes which are responsible for the undesirable side effects mentioned heretofore. The most desirable anti-inflammatory medication would inhibit AP-1 without activating GRE.

Steroids, such as dexamethasone and prednisone have been found to exhibit potent antiinflammatory activity, but also exhibit the previously-mentioned side effects.

Heretofore there has been no antiinflammatory agent found which does not cause side effects. Thus, new chemical agents are needed which would have the desired antiinflammatory effect without causing the side effects mentioned above.

Prior art compounds which relate to the triphenylcydopropyl and triphenylpropyl compounds of the invention are as follows: U.S. Pat. No. 3,941,833 (Gognaco) describes certain amino derivatives of 2,2-diaryl-cyclopropane. They are described as being useful for the treatment of disorders of the cardiovascular system. They are intended for systemic use. There is no indication in this patent that such compounds can or should be administered topically. Nor is there any indication that such compounds would be useful for treating inflammation of the skin.

Gilbert, et al. in *J. Med. Chem.* 1983, 26, 693–699 report triphenylpropylidene amines and nitriles as inhibitors of prostaglandin synthetase Blank et al. in *J. Med. Chem.* 1969, 12, 873–876 describe the inhibition by 2,3,3-triphenylpropylamines of the biosynthesis of aldosterone without altering deoxycorticosterone or corticosterone levels.

Schultz et al. in *J. Med. Chem.* 1967, 10, 717–724 describe diphenylpropanamides which are hypocholesteremic in rats and inhibit penicillin excretion in dogs.

Burch et al. in *Proc. Natl. Acad. Sci. USA* 1991, 88, 355–359 describe fluorenyl propanamides which inhibit localized inflammatory reactions in mice.

German Patent No. 2,726,993 (Gognaco) describes 1-substituted 2,2-diphenylcydopropanes. The patent indicates that they are useful as vasodilators and blood pressure lowering agents. They are intended for systemic use. There is no indication in this patent that such compounds can or should be administered topically. Nor is there any indication that such compounds would be useful for treating inflammation of the skin.

Belgian patent No. BE 855689 (Hexachemie S. A. Fr.) describes 2,2-diphenylcyclopropylmethylamides with vasodilator activity.

Precigoux, et al. describe the compound 4,4'-(3Acetemido-2-phenylpropylidene) diphenol diacetate in Acta Crystallogr., Sect. C. Cryst. Struct. Commun., C41 (8), 1985, pp. 1244–1246.

Falkenstein et al. describe certain phenylaziridine compounds in "Single electron transfer versus nucleophilic ring opening in reactions of cis-trans pairs of activated 2-phenylaziridines. Strong influence of nitrogen pyramid for N-benzoylaziridines", *J. Org. Chem.*, 1993, 58, pp. 7377–7381.

Stamm et al. describe other aziridines in "Reactions with aziridines. 53. Arene hydrides. 9. Intermediate substitution in the formation of a benzylic anion by an aromatic radical anion as observed with 1-benzoyl-2-phenylaziridine." *Chem. Ber.*, 1990, 123, pp. 2227–2230. Stamm et al. also described related aziridine structures in "Reductive ring opening of N-benzoylaziridine by anthracene hydride (anion of 9,10-dihydroanthracene) via base-induced fragmentation of the intermediate carbonyl adduct." *J. Org. Chem.*, 1989, 54, pp. 1603–1607. However, none of these publications describe the structures of this invention nor do they indicate that such compounds would be useful in treating inflammation.

Therefore, it is an object of this invention to provide one or more compounds capable of treating inflammatory diseases.

It is a further object of this invention to provide compounds capable of treating inflammatory diseases without causing side effects similar to those caused by glucocorticoids.

It is yet another object of this invention to provide a method of making compounds for treating inflammatory diseases.

Another object of this invention is to provide a method of treating inflammatory diseases in mammals by administration of the compounds of this invention.

SUMMARY OF THE INVENTION

This invention relates to novel non-steroidal small molecule organic compounds that exhibit the beneficial therapeutic properties of glucocorticoids, that may be free of glucocorticoid-like side effects, and which may have a high affinity for the human glucocorticoid receptor (hGR). The compounds of this invention have the following structure (I):

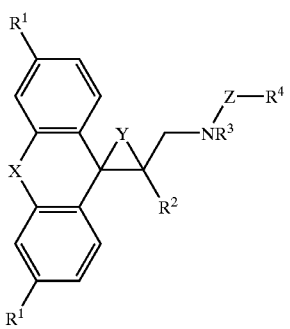

(I)

wherein X, $R^1$, $R^2$, $R^3$, $R^4$, $R^5$, W, Y and Z are as defined hereinafter. These compounds are useful in treating inflammatory diseases in humans and other mammals. The compounds of the present invention may also be useful in the treatment of other disorders, such as chronic adrenocortical disorder and hyperfunction, allergies, rheumatoid arthritis, lupus, use as immunosuppressants in organ transplant, pneumonia, bronchial asthma, hematological disorders, dermatitis and eczema. The present invention is also directed to pharmaceutical compositions containing the compounds of formula I and methods of treating inflammation and other conditions employing such compounds.

As used herein unless otherwise noted, alkyl and alkoxy, whether used along or as part of a substituent group, include straight and branched chains. For example, alkyl radicals include methyl, ethyl, propyl, isopropyl, n-butyl, isobutyl, sec-butyl, t-butyl, n-pentyl, 2-pentyl, 2-methylbutyl, neopentyl, n-hexyl, 2-hexyl, 2-methylpentyl, etc. Alkoxy radicals are oxygen ethers formed from the previously described straight or branched chain alkyl groups. Of course, if the alkyl or alkoxy substituent is branched there must be at least three carbon atoms in the group.

The term "aryl" as used herein along or in combination with other terms indicates aromatic hydrocarbon groups such as phenyl or naphthyl. The term heteroaryl means aromatic groups, incorporating as part of the aromatic ring, 1 or 2 hetero atoms selected from any of S, O, or N. With reference to substituents, the term "independently" means that when more than one of such substituent is possible such substituents may be the same or different from each other.

DETAILED DESCRIPTION OF THE PREFERRED EMBODIMENTS

The present invention is directed to compounds of the general formula I:

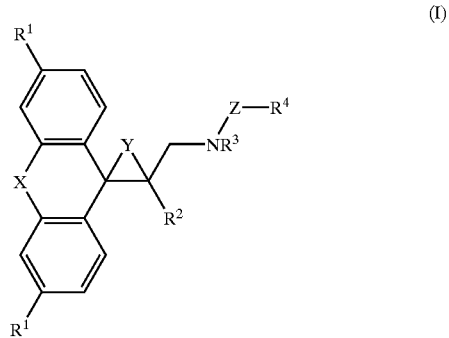

(I)

X may be a single bond or is chosen from hydrogen, sulfur or $NR^5$; wherein $R^5$ is selected from the group consisting of: hydrogen, alkyl; cycloalkyl; alkenyl; alkynyl; phenyl, in which said phenyl group is substituted with hydrogen or from one to three substituent groups each selected from the group consisting of lower alkyl ($C_2$–$C_6$), lower alkoxy, hydroxy, halo, carboxy, carboalkoxy, amino, amido, sulfonamido, or nitrile; phenyl lower alkyl in which said phenyl group is substituted with hydrogen or with from one to three substituent groups each selected from the group consisting of lower alkyl, lower alkoxy, hydroxy, halo, carboxy, carboalkoxy, amino, amido, sulfonamido or nitrile. X may further be selected from —$(CH_2)_n$— wherein n is an integer from 1 to 3; —HC═CH—; and —$CH_xW$ wherein W may be oxygen, sulfur or $NR^5$. Of course when X is hydrogen, it does not represent a connection between the phenyl rings;

wherein $R^1$ is from one to three substituent groups each selected from the group consisting of lower alkyl ($C_2$–$C_6$), lower alkoxy, hydroxy, halogen such as chlorine, fluorine, iodine or the like, carboxy, carboalkoxy, amino, amido, sulfonamido or nitrile;

wherein $R^2$ is a phenyl group in which said phenyl group is substituted with hydrogen or from one to three substituent groups each selected from the group consisting of lower alkyl($C_2$–$C_6$), lower alkoxy, hydroxy, halo, carboxy, carboalkoxy, amino, amido, sulfonamido or nitrile; or a heteroaromatic ring such as substituted- or unsubstituted thiophene, furan, pyrrole, pyridine, or the like;

wherein Y is —$CH_2$— or hydrogen;

wherein $R^3$ is chosen from the group consisting of hydrogen; alkyl; cycloalkyl; alkenyl; alkynyl; phenyl in which said phenyl group is substituted with hydrogen or from one to three substituent groups each selected from the group consisting of lower alkyl, lower alkoxy, hydroxy, halo, carboxy, carboalkoxy, amino, amido, sulfonamido or nitrile; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido or nitrile;

wherein Z is selected from the group consisting of carbonyl; carboxy; carbonylamino; or sulfone;,and wherein $R_4$ is straight- or branched-chain alkyl having from 2 to 12 carbon atoms; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido or nitrile; a heteroaromatic ring such as substituted- or unsubstituted thiophene, furan, pyrrole, pyridine, or the like or a heteroaromatic ring connected by a lower alkyl chain wherein said heteroaromatic ring is chosen from substituted- or unsubstituted thiophene, furan, pyrrole, pyridine or the like. When X is hydrogen, S or $NR^5$, $R^4$ may be phenyl wherein said phenyl group is substituted with hydrogen or with one to three substituent groups each selected from the group consisting of lower alkyl, lower alkoxy, hydroxy, halo, carboxy, carboalkoxy, amino, amido, sulfonamido or nitrile.

Preferably, the compounds of this invention have formula (I) above wherein X is hydrogen and Y is hydrogen. Also preferable are the compounds of this invention wherein $R^1$ is selected from the group consisting of hydrogen and halogen. More preferably, $R^1$ is fluorine.

More preferably, the compounds of this invention have formula (I) above wherein X is hydrogen, Y is hydrogen, $R^1$ is selected from the group consisting of hydrogen and halogen and $R^2$ is selected from the group consisting of phenyl, halophenyl, or methylenedioxy. Most preferably, $R^1$ is fluorine or hydrogen and $R^2$ is 4-chlorophenyl, 4-Iodophenyl or 3,4-methylendioxyphenyl.

Also preferable are compounds of formula (I) wherein X is hydrogen, Y is hydrogen, $R^1$ is selected from the group consisting of hydrogen and halogen, $R^2$ is selected from the group consisting of phenyl, halophenyl, or alkoxyphenyl and $R^3$ is selected from the group consisting of hydrogen and lower alkyl. Most preferably, $R^3$ is hydrogen.

Another preferable group of compounds of formula (I) are those wherein X is hydrogen, Y is hydrogen, $R^1$ is selected from the group consisting of hydrogen and halogen, $R^2$ is selected from the group consisting of phenyl and halophenyl, $R^3$ is selected from the group consisting of hydrogen and lower alkyl and Z is carbonyl. Preferably, $R^4$ is selected from the group consisting of straight-chain alkyl, phenyllower alkyl and heteroaromatic lower alkyl. Even more preferably $R^4$ is a heteroaromatic lower alkyl group. Most preferably, $R^4$ is 2-thiophenemethylene or 4chlorophenylmethylene.

The compounds of this invention are useful in treating inflammatory diseases such as rheumatoid arthritis, osteoarthritis, inflammatory bowel disease, dermatitis, and eczema. They may also be therapeutically beneficial in the treatment of other disorders including lupus, chronic adrenal disorder and hyperfunction, allergies, pneumonia, bronchial asthma, hematological disorders and as immunosuppressants in organ transplant. They may be administered topically or systemically.

The compounds of this invention have been found to bind to the hGR. However, because they differ in structure from glucocorticoids, they appear to bind selectively to the hGR, without binding to DNA and activating the GRE. This results in a potentially much lower incidence of side effects, and, consequently, longer periods of administration with greater overall efficacy and relief.

The compounds of this invention are optically active. The beneficial therapeutic activity may reside with either enantiomer or they may be most active and advantageously utilized in racemic mixtures.

Examples of particularly preferred compounds include: 98, 29, 33, 72, 90, 96, 84, 80, 47, 97, 123, 127, 128, 132, 140, 141, 145, 147, 150, 153, 165, 167, 173, 174, 175, 176, 177, 178, 179, and 180. Exemplary compounds are as follows:

N-(2-thiophrne)acetyl-2,3,3-triphenylpropylamine.

N-(5-methylthiopene)acetyl-2-phenyl-3,3-bis(4-fluorophenyl)propylamine.

N-(3-indolyl)acetyl-2,3,3-tiphenylpropylamine.

N-(2-carbonyl-5methylthiophene)-2(9H-fluoreny-9-yl)2-phenylethylamine.

N-(2chlorophenyl)acetyl-1,2,2-triphenylcyclopropylmethylamine.

N-(2-thienyl)carbonyl-1,2,2-triphenylcydopropylmethylamine.

N-(phenyloxy)carbonyl-1,2,2-triphenylcyclopropylmethylamine.

N-(4-chlorophenyloxy)carbonyl-1,2,2-triphenylcyclopropylmethylamine.

N-(2-pyridine)acetyl-2-(3,4-methylenedioxyphenyl)3,3-diphenylpropylamine.

N-(4n-butoxyphenyl)acetyl-2-(3,4-methylenedioxyphenyl)-3,3-diphenylpropylamine.

N-(2,4-difluorophenyl)acetyl-2-(3,4-methylenedioxyphenyl)-3,3-diphenylpropylamine.

N-(2-thiophene)carbonyl-2-(3,4-methylenedioxyphenyl)-3,3-diphenylpropylamine.

N-(3-cyanophenyl)acetyl-2-(3,4-methylenedioxyphenyl)-3,3-diphenylproylamine.

N-(2,4-difluorophenyl)carbonyl-2-(3,4-methylenedioxyphenyl)-3,3-diphenylpropylamine.

N-(4-fluorophenyl)acetyl-2-(3,4-methylenedioxyphenyl)-3,3-diphenylpropylamine.

N-(4,5-dichlorophenyl)carbonyl-2-(3,4-methylenedioxyphenyl)3,3-diphenlpropylamine.

N-(3-methylphenyl)acetyl-2-(4-trifluoromethylphenyl)-3,3-diphenylpropylamine.

N-(phenyl)acetyl-2-(4-trifluoromethylphenyl)-3,3-diphenylpropylamine.

N-(5-chloro-2-benzothiophene)acetyl-2-(4-trifluoromettylphenyl)-3,3-diphenylpropylamine.

N-(2,4difluorophenyl)carbonyl-2-(4-trifiuoromethylphenyl)-3,3-diphenylpropylamine.

N-(4-trifluormethylphenyl)acetyl-2-(4-trifluoromethylphenyl)-3,3-diphenylpropylamine.

N-(phenyl)acetyl-2(4-trifluoromethylphenyl)-3,3-diphenylpropylamine.

N-(4-fluorophenyl)acetyl-2-(4-iodomethylphenyl)-3,3-diphenylpropylamine.

N-(3,5-bis-trifluorophenyl)carbonyl-2-(4-iodomethylphenyl)3,3-diphenylpropylamine.

N-(4-chlorophenyl)carbonyl-2-(4-iodomethylphenyl)-3,3-diphenylpropylamine.

N-(3,4-dichlorophenyl)carbonyl-2-(4-iodomethylphenyl)3,3-diphenylpropylamine.

N-(2-fluorophenyl)carbonyl-2-(4-iodomethylphenyl)-3,3-diphenylpropylamine.

N-(2-fluorophenyl)carbonyl-2-(4-iodomethylphenyl)-3,3-diphenylpropylamine.

N-(4-(fluorophenyl)carbonyl-2-(4-iodomethylphenyl)3,3-diphenylpropylamine.

N-(4-trifluoromethylphenyl)carbonyl-2-(4-iodomethylphenyl)-3,3-diphenylpropylamine.

N-(3,5-bistrifluoromethylphenyl)carbonyl-2-(4-iodomethylphenyl)-3,3-diphenlpropylamine.

N-(2-thiophene)carbonyl-2-(4-iodomethylphenyl)3,3-diphenylpropylamine.

N-(5methyl-2-thiophene)carbonyl-2-(4-iodomethylphenyl)-3,3-diphenylpropylamine.

N-(4chlorophenyl)carbonyl-2-(3,4-methylenedioxyphenyl3,3-diphenlpropylamine.

N-(2-propyl)carbonyl-1,2,2-triphenylcydopropylmethylamine.

The compounds of this invention may also include the respective hydrates of compounds specifically identified herein.

The compounds of formula I may be prepared according to the following reaction schemes.

Reaction Scheme 1 displays a method of making the compounds of formula I, where $R^1$–$R^5$, W, X, Y and Z are as defined above. Treatment of a suitable substituted or unsubstituted diphenyl methyl-, fluorenyl-, or 10,11-dihydro-5H-dibenzo[1,d]cyclohepten-4-yl chloride or bromide with an aryl- or heteroaryl acetonitrile using n-BuLi and the like or phase-transfer conditions, afford nitrile intermediates of structure A Reduction of A with LAH, $NaBH_4$/$BH_3$ and the like leads to the formation of amines C. Treatment of structure A with methylene chloride in the presence of potassium amide/liquid ammonia leads to the formation of structure B. Reduction of the nitrile group of structure B with LAH, $NaBH_4$/$BH_3$ and the like leads to an amine of structure. By reacting C or D with acid chlorides as set forth below in Scheme I in combination with bases such as NaOAc and the like, organic acids in combination with activating agents such as 1,1'-carbonyldiimidazole and the like, sulfonyl chlorides, chloroformates, isocyanates, isothiocyanates, or a suitable organic sulfonyl chloride, compounds of structure I are obtained. Optionally, nitrites of structure A, when treated with diisobutylaluminum hydride (DiBAL), are converted to aldehydes of structure E. Treatment of E with Rink resin affords resin-bound imines of structure F which are reduced with sodium triacetoxy borane to resin-bound imines of structure G. Treatment of G with an appropriate acid in the presence of O-(7-azabenzotriazol-1-yl)-N,N,N',N'-tetramethyluronium hexafluorophosphate (hereinafter referred to as "HATU") and diisopropylethylamine (DIEA) affords compounds of structure I. Compounds of structure I may also be prepared by the reaction of amines of structure H with appropriate carboxylic acids in the presence of resin-bound 1(3-dimethylaminopropyl)-3-ethylcarbodiimide which is prepared from 1-(3-dimethylaminopropyl)-3-ethylcarbodiimide and Merrifield resin.

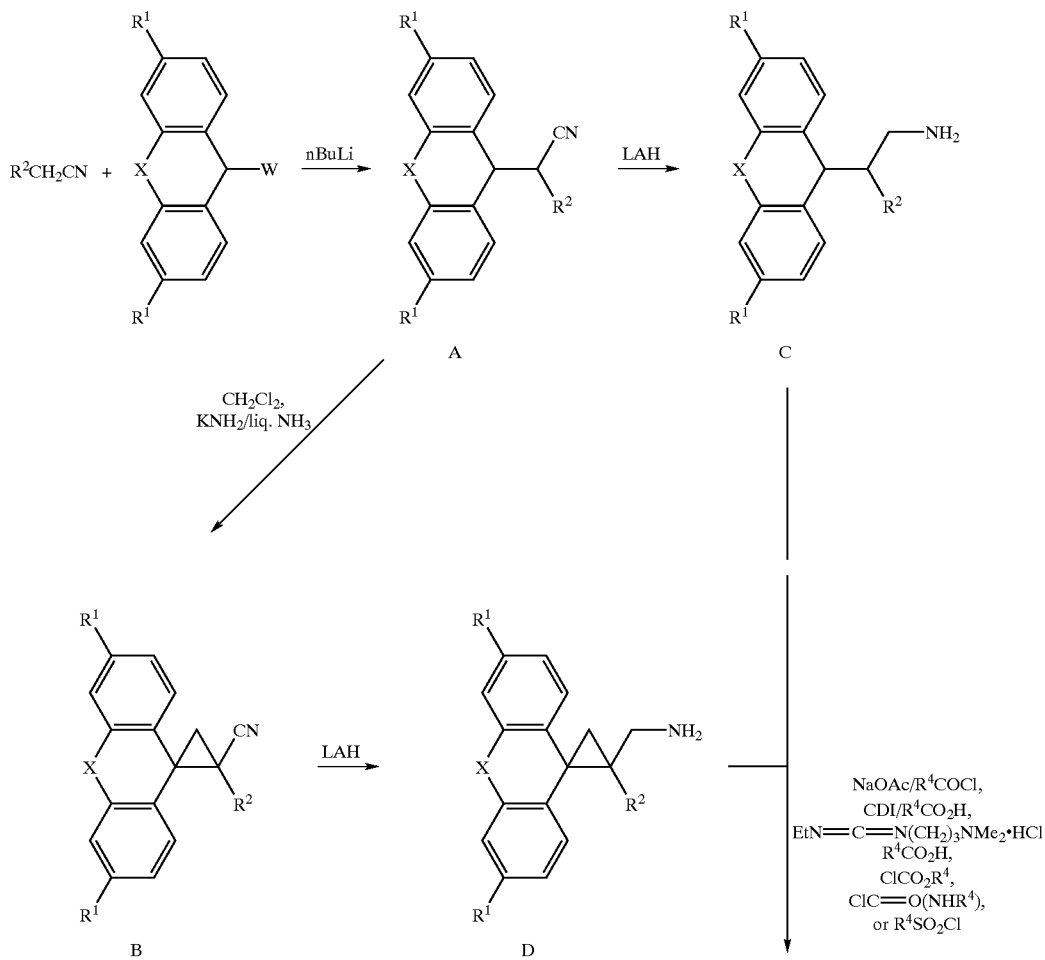

Scheme 1

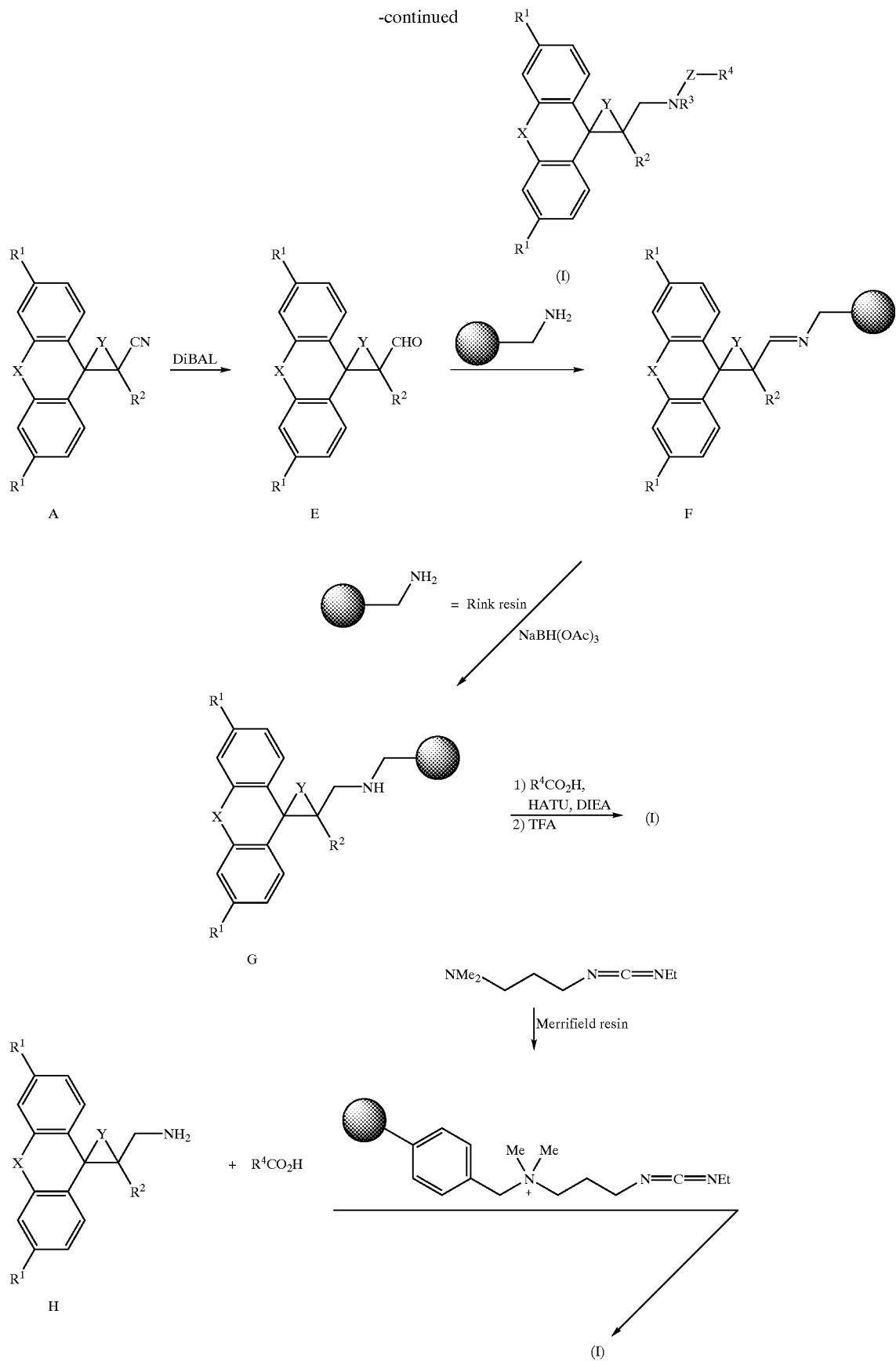

To prepare the pharmaceutical compositions of this invention, one or more compounds or salts thereof of the invention, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations, such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 50 to about 100 mg of the active ingredient, although other unit dosages may be employed. The compounds of this invention may also be applied or utilized topically. If the delivery parameters of the topically active pharmaceutical or cosmetic agent so require, the topically active composition of this invention may preferably be freer composed of a pharmaceutically or cosmetically acceptable vehicle capable of functioning as a delivery system to enable the penetration of the topically active agent into the skin. In alternative embodiments, the topically active pharmaceutical or cosmetic composition may be optionally combined with other ingredients such as moisturizers, foaming agents, cosmetic adjuvants, anti-oxidants, surfactants, foaming agents, conditioners, humectants, fragrances, viscosifiers, buffering agents, preservatives, and the like in an amount which will not destroy the active ingredient in order to produce cosmetic or pharmaceutical products.

The topically active pharmaceutical or cosmetic composition should be applied in an amount effective to treat inflammation of mammalian skin. As used herein "amount effective" shall mean an amount sufficient to ameliorate inflammation of mammalian skin. A composition containing 0.001–10.0% of active agent is applied to the skin surface when amelioration of an inflammatory condition is desired. Preferably, a composition containing 0.05–5.0% of active agent is applied to the skin surface such that, based

TABLE 1

Physical and Biological Properties of Triphenylpropylamine and Triphenylcyclopropyl amine Derivatives

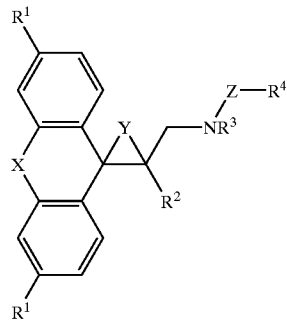

| cmp | $R^1$ | $R^2$ | $R^3$ | $R^4$ | X | Y | Z | mp,° C. | hGR $IC_{50}$ (nM) | hPR % inh 10 µM |
|---|---|---|---|---|---|---|---|---|---|---|
| 1 | H | Ph | H | PhCH$_2$ | H, H | H, H | CO | 146.0–147.0 | 890 | −0.2 |
| 2 | H | Ph | H | 2-ClPhCH$_2$ | H, H | H, H | CO | 140.5–141.2 | 134 | −23 |
| 3 | H | Ph | H | 4-ClPhCH$_2$ | H, H | H, H | CO | 168.4–170.9 | 480 | 4 |
| 4 | H | Ph | H | 4-MePhCH$_2$ | H, H | H, H | CO | 142.3–143.6 | 528 | 12 |
| 5 | H | Ph | H | 2-MeOPhCH$_2$ | H, H | H, H | CO | 156.9–158.9 | 62% | |
| 6 | H | Ph | H | 4-MeOPhCH$_2$ | H, H | H, H | CO | 157–159 | 910 | |
| 7 | H | Ph | H | 3,4-MeOPhCH$_2$ | H, H | H, H | CO | 123–124.5 | 910 | 11.6 |
| 8 | H | Ph | H | 2,6-diClPhCH$_2$ | H, H | H, H | CO | 165.2–166.5 | 340 | 3 |
| 9 | H | Ph | H | 3,4-diClPhCH$_2$ | H, H | H, H | CO | 65–68 | 1480 | |
| 10 | H | Ph | H | 2-CF$_3$PhCH$_2$ | H, H | H, H | CO | 109–111.5 | 780 | 15 |
| 11 | H | Ph | H | 3-CF$_3$PhCH$_2$ | H, H | H, H | CO | 108.8–111.3 | 830 | 20 |
| 12 | H | Ph | H | 4-CF$_3$PhCH$_2$ | H, H | H, H | CO | 119.5–120.3 | 1500 | 15 |
| 13 | H | Ph | H | Ph$_2$CH | H, H | H, H | CO | 178.7–179.8 | 780 | |
| 14 | H | 4-ClPh | H | PhCH$_2$ | H, H | H, H | CO | 151.5–152.7 | 72 | 18 |
| 15 | 4-F | Ph | H | PhCH$_2$ | H, H | H, H | CO | 87.5–89.7 | 21 | |
| 16 | 4-F | Ph | H | 2-ClPhCH$_2$ | H, H | H, H | CO | 127.3–129.4 | 45 | |
| 17 | 4-F | Ph | Me | PhCH$_2$ | H, H | H, H | CO | 86.9–88.2 | | |
| 18 | H | Ph | H | Ph | H, H | H, H | CO | 161.5–163 | 610 | 14.1 |
| 19 | H | Ph | H | Ph(CH$_2$)$_2$ | H, H | H, H | CO | 107.4–109.0 | 141 | 24 |
| 20 | H | Ph | H | 2-MeoPh(CH$_2$)$_2$ | H, H | H, H | CO | 137–140 | 58 | 9 |
| 21 | H | 4-ClPh | H | 2-MeOPh(CH$_2$)$_2$ | H, H | H, H | CO | 122.2–123.5 | 57 | 21 |
| 22 | H | Ph | H | 2-ClPh(CH$_2$)$_2$ | H, H | H, H | CO | 135.0–135.8 | 103 | |
| 23 | 4-F | Ph | H | 2-MeOPh(CH$_2$)$_2$ | H, H | H, H | CO | 78.9–80.9 | 22 | |

TABLE 1-continued

Physical and Biological Properties of Triphenylpropylamine and Triphenylcyclopropyl amine Derivatives

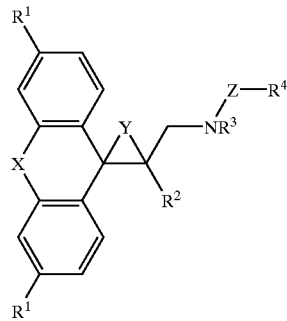

| # | X | R¹ | Y | R² | R¹,R¹ | R³,R³ | Z | mp (°C) | col1 | col2 |
|---|---|---|---|---|---|---|---|---|---|---|
| 24 | H | Ph | H | Ph(CH₂)₃ | H, H | H, H | CO | 78.1–81.0 | 670 | 10 |
| 25 | H | Ph | H | PhCH₂ | H, H | H, H | SO₂ | 172.9–174.2 | 210 | |
| 26 | H | Ph | H | 4-MePh | H, H | H, H | SO₂ | 139.7–142.1 | 175 | |
| 27 | H | Ph | H | PhSO₂CH₂ | H, H | H, H | CO | 186.9–187.5 | 67 | |
| 28 | H | Ph | H | 4-MePhSO₂CH₂ | H, H | H, H | CO | 190.3–191.9 | 57 | |
| 29 | H | Ph | H | 2-thiopheneCH₂ | H, H | H, H | CO | 130–132 | 8 | 28.3 |
| (+) | | | (+) | | | | | | 24 | |
| (−) | | | (−) | | | | | | >800 | |
| 30 | H | Ph | H | 5-Me-2-thiophene | H, H | H, H | CO | 183.5–185 | 50 | |
| 31 | 4-F | Ph | H | 2-thiopheneCH₂ | H, H | H, H | CO | 84.9–85.3 | 8 | |
| 32 | 4-F | Ph | H | 5-Me-2-thiopheneCH₂ | H, H | H, H | CO | 127.9–128.9 | 7 | |
| 33 | H | 4-IPh | H | 2-thiopheneCH₂ | H, H | H, H | CO | 127–130 | 8.6 | |
| 34 | H | 4-ClPh | H | 2-thiopheneCH₂ | H, H | H, H | CO | 126.3–127.0 | 21 | 17 |
| 35 | H | 4-ClPh | H | 3-thiopheneCH₂ | H, H | H, H | CO | 126.4–127.9 | 54 | |
| 36 | H | Ph | H | 3-thiopheneCH₂ | H, H | H, H | CO | 135–138 | 25 | 22 |
| 37 | H | Ph | H | 2-thiophene(CH₂)₃ | H, H | H, H | CO | 105.5–106.9 | 500 | 4 |
| 38 | H | Ph | H | 2-thiopheneCH=CH(t) | H, H | H, H | CO | 217.3–218.9 | 189 | |
| 39 | H | Ph | H | 3-thiopheneCH=CH | H, H | H, H | CO | 204.8–206.5 | 727 | |
| 40 | H | Ph | H | 2-thiophene | H, H | H, H | SO₂ | 169.0–170.9 | 151 | 22 |
| 41 | H | 4-ClPh | H | 2-thiophene | H, H | H, H | SO₂ | 180.4–181.9 | 491 | |
| 42 | H | Ph | H | 3-thiophene | H, H | H, H | CO | 153.5–154.7 | 68 | 18 |
| 43 | H | Ph | H | 2-benzothiophene | H, H | H, H | CO | 218.3–218.8 | 495 | |
| 44 | H | Ph | Me | 2-thiopheneCH₂ | H, H | H, H | CO | 107–109.3 | 133 | |
| 45 | H | Ph | H | 2-thiophene | H, H | H, H | CO | 139–142 | 31 | 5 |
| 46 | H | 2-thio | H | 2-thiopheneCH₂ | H, H | H, H | CO | 138.2–139.9 | 723 | |
| 47 | H | Ph | H | 3-indoleCH₂ | H, H | H, H | CO | 89–93 | 416 | 17 |
| 48 | H | Ph | H | 3-indole(CH₂)₂ | H, H | H, H | CO | 100–114 | 605 | 19 |
| 49 | H | Ph | H | 2-pyridylCH₂ | H, H | H, H | CO | 120.1–121.7 | 200 | 11 |
| 50 | H | Ph | H | NHPh | H, H | H, H | CO | 205–206 | | |
| 51 | H | Ph | H | 2-MeOPhNH | H, H | H, H | CO | 203–204 | 32% | |
| 52 | H | Ph | H | 2-ClPhNH | H, H | H, H | CO | 210–211 | 273 | |
| 53 | H | Ph | H | 2-FPhNH | H, H | H, H | CO | 190–191 | 293 | |
| 54 | H | Ph | H | PhCH₂NH | H, H | H, H | CO | 170–171 | 219 | |
| 55 | H | Ph | H | 2,4-diClPhCH₂NH | H, H | H, H | CO | 166–167 | 121 | |
| 56 | H | Ph | H | PhO | H, H | H, H | CO | 128–129 | 310 | |
| 57 | H | Ph | H | 4-ClPhO | H, H | H, H | CO | 159–160 | 294 | |
| 58 | H | Ph | H | 4-FPhO | H, H | H, H | CO | 150–151 | 240 | |
| 59 | H | Ph | H | 2-NapthO | H, H | H, H | CO | 151–152 | 155 | |
| 60 | H | Ph | H | Pr | H, H | H, H | CO | 88–89 | 446 | |
| 61 | H | Ph | H | i-Pr | H, H | H, H | CO | 114–115 | 584 | |
| 62 | H | Ph | H | n-Bu | H, H | H, H | CO | 78–79 | 121 | |
| 63 | H | Ph | H | i-Bu | H, H | H, H | CO | 112–113 | 316 | |
| 64 | H | Ph | H | t-Bu | H, H | H, H | CO | 143–144 | 296 | |
| 65 | H | Ph | H | CH₂CO₂Et | H, H | H, H | CO | 103–105.5 | 937 | |
| 66 | H | Ph | H | PhCH₂ | SB | H, H | CO | 148.7–150.8 | 888 | 18 |
| 67 | H | Ph | H | 2-MeOPhCH₂ | SB | H, H | CO | 159.4–161.1 | 23% | |
| 68 | H | Ph | H | 2-ClPhCH₂ | SB | H, H | CO | 162.4–164.2 | 46% | |
| 69 | H | Ph | H | 2-CF₃PhCH₂ | SB | H, H | CO | 153.9–155 | 15% | |
| 70 | H | Ph | H | 2-MeOPh(CH₂)₂ | SB | H, H | CO | 173.5–175.6 | 53% | |
| 71 | H | Ph | H | 2-thiopheneCH₂ | SB | H, H | CO | 128.7–130.5 | 820 | 16 |
| 72 | H | Ph | H | 5-Me-2-thiophene | SB | H, H | CO | 158.3–160.5 | 33% | |
| 73 | H | Ph | H | PhCH₂ | (CH₂)₂ | H, H | CO | 172.7–174.6 | 770 | |
| 74 | H | Ph | H | 2-MeOPh(CH₂)₂ | (CH₂)₂ | H, H | CO | 134.3–136.8 | 388 | |
| 75 | H | Ph | H | 2-thiopheneCH₂ | (CH₂)₂ | H, H | CO | 175–177.5 | 363 | |
| 76 | H | Ph | H | 3-thiopheneCH₂ | (CH₂)₂ | H, H | CO | 167.3–169.3 | 571 | |
| 77 | H | Ph | H | 5-Me-2-thiophene | (CH₂)₂ | H, H | CO | 172.1–173 | 882 | |
| 78 | H | Ph | H | PhCH₂ | H, H | CH₂ | CO | 150–152 | 1200 | 6 |
| 79 | H | Ph | H | 3,4-MeOPhCH₂ | H, H | CH₂ | CO | 131–133.5 | 1000 | 24.5 |
| 80 | H | Ph | H | 2-ClPhCH₂ | H, H | CH₂ | CO | 128.5–130.5 | 955 | −11 |
| 81 | H | Ph | H | 2-MeOPh(CH₂)₂ | H, H | CH₂ | CO | 187.5–189 | 709 | |

TABLE 1-continued

Physical and Biological Properties of Triphenylpropylamine and Triphenylcyclopropyl amine Derivatives

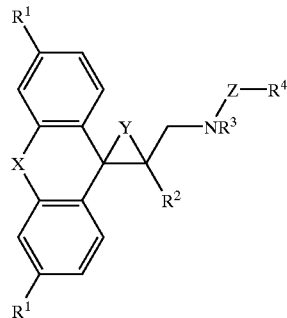

| Cmpd | R¹ | R² | R³ | R⁴ | X | Y | Z | m.p. | Molecular Ion | % Inhibition MOCH |
|---|---|---|---|---|---|---|---|---|---|---|
| 82 | H | Ph | H | CHPh₂ | H, H | CH₂ | CO | 166–169 | 510 | −20.4 |
| 83 | H | Ph | H | n-propyl | H, H | CH₂ | CO | 149–150 | 573 | 45 |
| 84 | H | Ph | H | i-propyl | H, H | CH₂ | CO | 167–168 | 612 | 15.3 |
| 85 | H | Ph | H | 2-Me-propyl | H, H | CH₂ | CO | 142–143 | 68% | 7.2s |
| 86 | H | Ph | H | t-butyl | H, H | CH₂ | CO | 121–122 | 665 | 12.6 |
| 87 | H | Ph | H | n-butyl | H, H | CH₂ | CO | 122–123 | 681 | 19.8 |
| 88 | H | Ph | H | 2-thiopheneCH₂ | H, H | CH₂ | CO | 135–137 | 425 | |
| 89 | H | Ph | H | 3-thiopheneCH₂ | H, H | CH₂ | CO | 130–135 | 570 | 22 |
| 90 | H | Ph | H | 2-thiophene | H, H | CH₂ | CO | 152.5–155 | 612 | |
| 91 | H | Ph | H | 5-Me-2-thiophene | H, H | CH₂ | CO | 168–170.5 | 421 | |
| 92 | H | Ph | H | PhNH | H, H | CH₂ | CO | 209–210 | 1488 | −1 |
| 93 | H | Ph | H | 2-FPhNH | H, H | CH₂ | CO | 235–236 | 17% | 33.9 |
| 94 | H | Ph | H | 2-MeOPhNH | H, H | CH₂ | CO | 246–247 | 13% | −18.6 |
| 95 | H | Ph | H | PhCH₂NH | H, H | CH₂ | CO | 231–232 | 4% | −14.3 |
| 96 | H | Ph | H | PhO | H, H | CH₂ | CO | 146–147 | 927 | 9.9 |
| 97 | H | Ph | H | 4-ClPhO | H, H | CH₂ | CO | 171–172 | 157 | 12.5 |

| Cmpd | R¹ | R² | R³ | R⁴ | X | Y | Z | Mass | Molecular Ion | % Inhibition MOCH |
|---|---|---|---|---|---|---|---|---|---|---|
| 98 | H | 3,4-(OCH₂O)Ph | H | 4-ClPhCH₂ | H, H | H, H | CO | 484.0 | 486 | |
| 99 | H | 3,4-(OCH₂O)Ph | H | 2-thiopheneCH₂ | H, H | H, H | CO | 455.6 | 458 | 35 |
| 100 | H | 3,4-(OCH₂O)Ph | H | 3-Me-5-Cl-benzo-thiophene-2-CH₂ | H, H | H, H | CO | 554.1 | 554, 556 | 18 |
| 101 | H | 3,4-(OCH₂O)Ph | H | 5-Cl-benzo-thiophene-2-CH₂ | H, H | H, H | CO | 540.1 | 540, 542 | 26 |
| 102 | H | 3,4-(OCH₂O)Ph | H | 2-pyridineCH₂ | H, H | H, H | CO | 450.5 | 451 | 51 |
| 103 | H | 3,4-(OCH₂O)Ph | H | 3-CF₃phenylCH₂ | H, H | H, H | CO | 517.5 | 518 | 37 |
| 104 | H | 3,4-(OCH₂O)Ph | H | 3,5-di-CF₃phenylCH₂ | H, H | H, H | CO | 585.5 | 586 | 52 |
| 105 | H | 3,4-(OCH₂O)Ph | H | 4-NO₂phenylCH₂ | H, H | H, H | CO | 494.5 | 495 | 24 |
| 106 | H | 3,4-(OCH₂O)Ph | H | 4-BuOphenylCH₂ | H, H | H, H | CO | 521.7 | 522 | 52 |
| 107 | H | 3,4-(OCH₂O)Ph | H | 2-MeOphenylCH₂ | H, H | H, H | CO | 479.6 | 480 | 28 |
| 108 | H | 3,4-(OCH₂O)Ph | H | 3,5-di-MeOphenylCH₂ | H, H | H, H | CO | 509.6 | 510 | 38 |
| 109 | H | 3,4-(OCH₂O)Ph | H | phenylCH₂ | H, H | H, H | CO | 449.5 | 450 | 22 |
| 110 | H | 3,4-(OCH₂O)Ph | H | 3-FphenylCH₂ | H, H | H, H | CO | 467.5 | 468 | 20 |
| 111 | H | 3,4-(OCH₂O)Ph | H | 2,4-diF-phenylCH₂ | H, H | H, H | CO | 485.5 | 486 | 60 |
| 112 | H | 3,4-(OCH₂O)Ph | H | 2,4-di-Cl-phenylCH₂ | H, H | H, H | CO | 518.4 | 518, 520 | 36 |
| 113 | H | 3,4-(OCH₂O)Ph | H | 3,4-diCl-phenylCH₂ | H, H | H, H | CO | 518.4 | 518, 520 | 31 |
| 114 | H | 3,4-(OCH₂O)Ph | H | phenylthioCH₂ | H, H | H, H | CO | 481.6 | 482 | 41 |
| 115 | H | 3,4-(OCH₂O)Ph | H | 3-thiophene | H, H | H, H | CO | 441.5 | 442 | 28 |
| 116 | H | 3,4-(OCH₂O)Ph | H | 2-thiophene | H, H | H, H | CO | 441.5 | 442 | 62 |
| 117 | H | 3,4-(OCH₂O)Ph | H | phenyl | H, H | H, H | CO | 435.5 | 438 | 28 |
| 118 | H | 3,4-(OCH₂O)Ph | H | 2-MeO-phenyl | H, H | H, H | CO | 465.5 | 466 | 38 |
| 119 | H | 3,4-(OCH₂O)Ph | H | 2-indole | H, H | H, H | CO | 474.6 | 475 | 31 |
| 120 | H | 3,4-(OCH₂O)Ph | H | 3,5-di-CF₃phenyl | H, H | H, H | CO | 571.5 | 572 | 27 |
| 121 | H | 3,4-(OCH₂O)Ph | H | 3-NO₂-phenyl | H, H | H, H | CO | 480.5 | 481 | 10 |
| 122 | H | 3,4-(OCH₂O)Ph | H | 3-NO₂-4-Me-phenyl | H, H | H, H | CO | 494.5 | 495 | 33 |
| 123 | H | 3,4-(OCH₂O)Ph | H | 3-CN-phenyl | H, H | H, H | CO | 460.5 | 461 | 51 |
| 124 | H | 3,4-(OCH₂O)Ph | H | phenylethyl | H, H | H, H | CO | 463.6 | 464 | 35 |
| 125 | H | 3,4-(OCH₂O)Ph | H | 4-tBu-phenyl | H, H | H, H | CO | 491.6 | 492 | 31 |
| 126 | H | 3,4-(OCH₂O)Ph | H | 4-Me-phenyl | H, H | H, H | CO | 449.5 | 450 | 46 |
| 127 | H | 3,4-(OCH₂O)Ph | H | 2,4-diF-phenyl | H, H | H, H | CO | 471.5 | 472 | 61 |
| 128 | H | 3,4-(OCH₂O)Ph | H | 4-F-phenyl | H, H | H, H | CO | 453.5 | 454 | 54 |
| 129 | H | 3,4-(OCH₂O)Ph | H | 2-Cl-phenyl | H, H | H, H | CO | 470.0 | 470, 472 | 41 |
| 130 | H | 3,4-(OCH₂O)Ph | H | 4-Cl-phenyl | H, H | H, H | CO | 470.0 | 470, 472 | 37 |
| 131 | H | 3,4-(OCH₂O)Ph | H | 3,5-diCl-phenyl | H, H | H, H | CO | 504.4 | 504, 506 | 18 |
| 132 | H | 3,4-(OCH₂O)Ph | H | 4,5-diCl-phenyl | H, H | H, H | CO | 504.4 | 504, 506 | 69 |
| 133 | H | 3,4-(OCH₂O)Ph | H | 2-Me-phenyl | H, H | H, H | CO | 449.5 | 450 | 46 |
| 134 | H | 3,4-(OCH₂O)Ph | H | 4-biphenylCH₂ | H, H | H, H | CO | 525.6 | 526 | 29 |
| 135 | H | 4-CF₃-Ph | H | 2-thiopheneCH₂ | H, H | H, H | CO | 479.6 | 480 | 31 |

TABLE 1-continued

Physical and Biological Properties of Triphenylpropylamine and Triphenylcyclopropyl amine Derivatives

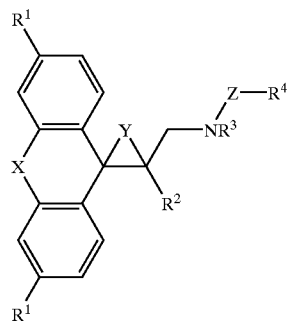

| | | | | | | | | | |
|---|---|---|---|---|---|---|---|---|---|
| 136 | H | 4-CF$_3$-Ph | H | 2-thiophene | H, H | H, H | CO | 465.5 | 466 | 38 |
| 137 | H | 4-CF$_3$-Ph | H | 2-Cl-phenyl | H, H | H, H | CO | 494 | 494, 496 | 45 |
| 138 | H | 4-CF$_3$-Ph | H | 3,4-diCl-phenylCH$_2$ | H, H | H, H | CO | 542.4 | 542, 544 | 33 |
| 139 | H | 4-CF$_3$-Ph | H | 2,4-diCl-phenyl | H, H | H, H | CO | 528.4 | 528, 530 | 42 |
| 140 | H | 4-CF$_3$-Ph | H | 3-Me-phenylCH$_2$ | H, H | H, H | CO | 487.6 | 488 | 57 |
| 141 | H | 4-CF$_3$-Ph | H | phenylCH$_2$ | H, H | H, H | CO | 473.5 | 474 | 66 |
| 142 | H | 4-CF$_3$-Ph | H | 2-pyridineCH$_2$ | H, H | H, H | CO | 474.5 | 475 | 39 |
| 143 | H | 4-CF$_3$-Ph | H | 4-MeS-phenylCH$_2$ | H, H | H, H | CO | 519.6 | 520 | 19 |
| 144 | H | 4-CF$_3$-Ph | H | 2-MeO-4-Cl-phenyl | H, H | H, H | CO | 524 | 524, 526 | 33 |
| 145 | H | 4-CF$_3$-Ph | H | 5-Cl-benzo-thiophene-2-CH$_2$ | H, H | H, H | CO | 564.1 | 564, 565 | 54 |
| 146 | H | 4-CF$_3$-Ph | H | 2-Cl-phenylCH$_2$ | H, H | H, H | CO | 508.0 | 508.2 | 39 |
| 147 | H | 4-CF$_3$-Ph | H | 2,4-diF-phenylCH$_2$ | H, H | H, H | CO | 509.5 | 510.2 | 55 |
| 148 | H | 4-CF$_3$-Ph | H | 2-MeO-phenylCH$_2$ | H, H | H, H | CO | 503.6 | 504 | 42 |
| 149 | H | 4-CF$_3$-Ph | H | 3,5-diMeO-phenylCH$_2$ | H, H | H, H | CO | 533.6 | 534 | 42 |
| 150 | H | 4-CF$_3$-Ph | H | 4-CF$_3$-phenylCH$_2$ | H, H | H, H | CO | 541.5 | 542 | 61 |
| 151 | H | 4-CF$_3$-Ph | H | 3,5-diCF$_3$-phenylCH$_2$ | H, H | H, H | CO | 609.5 | 610 | 41 |
| 152 | H | 4-CF$_3$-Ph | H | 4-Me-phenylCH$_2$ | H, H | H, H | CO | 487.6 | 488 | 41 |
| 153 | H | 4-CF$_3$-Ph | H | Ph$_2$CH | H, H | H, H | CO | 549.6 | 550 | 69 |
| 154 | H | 4-CF$_3$-Ph | H | 4-NO$_2$-phenylCH$_2$ | H, H | H, H | CO | 518.5 | 519 | 34 |
| 155 | H | 4-CF$_3$-Ph | H | 4-(Me$_2$N)-phenylCH$_2$ | H, H | H, H | CO | 516.6 | 517 | 29 |
| 156 | H | 4-CF$_3$-Ph | H | 4-biphenylCH$_2$ | H, H | H, H | CO | 549.6 | 550 | 19 |
| 157 | H | 4-CF$_3$-Ph | H | 2-naphthylCH$_2$ | H, H | H, H | CO | 523.6 | 524 | 10 |
| 158 | H | 4-CF$_3$-Ph | H | 5-Cl-3-Me-benzo-thiopheneCH$_2$ | H, H | H, H | CO | 578.1 | 578, 580 | 16 |
| 159 | H | 4-CF$_3$-Ph | H | 4-(Me$_2$N)-phenyl(CH)$_2$ | H, H | H, H | CO | 528.6 | 529 | 12 |
| 160 | H | 4-CF$_3$-Ph | H | 3,5-diCF$_3$phenyl | H, H | H, H | CO | 595.5 | 596 | 10 |
| 161 | H | 4-I-Ph | H | 2-Cl-phenylCH$_2$ | H, H | H, H | CO | 565.9 | 566, 568 | 42 |
| 162 | H | 4-I-Ph | H | 4-Cl-phenylCH$_2$ | H, H | H, H | CO | 565.9 | 566, 568 | 30 |
| 163 | H | 4-I-Ph | H | 3,4-diCl-phenylCH$_2$ | H, H | H, H | CO | 600.3 | 600 | 44 |
| 164 | H | 4-I-Ph | H | 2-F-phenylCH$_2$ | H, H | H, H | CO | 549.4 | 550 | 40 |
| 165 | H | 4-I-Ph | H | 4-F-phenylCH$_2$ | H, H | H, H | CO | 549.4 | 550 | 79 |
| 166 | H | 4-I-Ph | H | 4-CF$_3$-phenylCH$_2$ | H, H | H, H | CO | 599.4 | 600 | 46 |
| 167 | H | 4-I-Ph | H | 3,5-diCF$_3$-phenylCH$_2$ | H, H | H, H | CO | 667.4 | 668 | 63 |
| 168 | H | 4-I-Ph | H | 2-MeO-phenylCH$_2$ | H, H | H, H | CO | 561.5 | 562 | 32 |
| 169 | H | 4-I-Ph | H | 3-MeO-phenylCH$_2$ | H, H | H, H | CO | 561.5 | 562 | 45 |
| 170 | H | 4-I-Ph | H | 4-MeO-phenylCH$_2$ | H, H | H, H | CO | 561.5 | 562 | 25 |
| 171 | H | 4-I-Ph | H | 3,5-diMeO-phenylCH$_2$ | H, H | H, H | CO | 591.5 | 592 | 25 |
| 172 | H | 4-I-Ph | H | 2-Cl-phenyl | H, H | H, H | CO | 551.9 | 552 | 32 |
| 173 | H | 4-I-Ph | H | 4-Cl-phenyl | H, H | H, H | CO | 551.9 | 552 | 72 |
| 174 | H | 4-I-Ph | H | 3,4-diCl-phenyl | H, H | H, H | CO | 586.3 | 587 | 50 |
| 175 | H | 4-I-Ph | H | 2-F-phenyl | H, H | H, H | CO | 535.4 | 536 | 65 |
| 176 | H | 4-I-Ph | H | 4-F-phenyl | H, H | H, H | CO | 535.4 | 536 | 68 |
| 177 | H | 4-I-Ph | H | 4-CF$_3$-phenyl | H, H | H, H | CO | 585.4 | 586 | 53 |
| 178 | H | 4-I-Ph | H | 3,5-diCF$_3$-phenyl | H, H | H, H | CO | 653.4 | 654 | 53 |
| 179 | H | 4-I-Ph | H | 2-thiophene | H, H | H, H | CO | 523.4 | 524 | 53 |
| 180 | H | 4-I-Ph | H | 5-Me-2-thiophene | H, H | H, H | CO | 537.5 | 538 | 57 |
| 181 | H | 4-I-Ph | H | 2-MeO-phenyl | H, H | H, H | CO | 547.4 | 548 | 41 |
| 182 | H | 4-I-Ph | H | 3-MeO-phenyl | H, H | H, H | CO | 547.4 | 548 | 15 |
| 183 | H | 4-I-Ph | H | 3,5-diMeO-phenyl | H, H | H, H | CO | 577.5 | 578 | 42 | upon a square cm of skin surface, from about 2 μl /cm$^2$ to about 8 μl /cm$^2$ of topically active agent is present when amelioration of an inflammatory condition is desired.

The following examples are merely illustrative of the compounds, methods of making said compounds, compositions and methods of using said compounds and compositions, and do not serve to limit the scope of this invention.

EXAMPLE 1

2,3,3-Triphenylpropionitrile, (Hauser, C. R. et al., Formation and Preferential β-Alkylation of the Dicarbanion of 2,3,3-Triphenylpropionitrile by Means of Potassium Amide in Liquid Ammonia. *J. Amer. Chem. Soc.*, 1959, 81, 4099–4102) was made as follows. A solution of phenylacetonitrile (1.00 g, 0.0086 mol) and THF (17mL) was cooled to −78° C. in a dry ice-acetone bath and treated dropwise with a solution of n-butyllithium in hexane (3.80 mL, 0.0095 mol). After stirring for 45 minutes at −78° C., a solution of diphenyl methylchloride (1.75 g, 0.0086 mol) and THF was added dropwise to give a light yellow solution. After stirring at room temperature overnight, water (20 mL) and diethyl ether (50 mL) were added with vigorous stirring. The organic layer was separated, dried over anhydrous magnesium sulfate ($MgSO_4$), filtered, and evaporated to give an oil. This material was triturated and filtered to give 1,2,2-triphenylpropionitrile.

EXAMPLE 2

9H-4(Fluoren-9-yl)phenylacetonitrile was prepared using the same procedure as that described in Example 1, however, 9-bromofluorene was substituted for diphenylmethylchloride. 9H-(Fluoren-9-yl)phenylacetonitrile was obtained, having a melting point of 146–148.3° C.

EXAMPLE 3

(10,11-Dihydro-5H-dibenzo[1,d]cyclohepten-4-yl)phenylacetonitrile was made using the same procedure as described above in Example 1, with the exception that 5-chloro-10,11-dihydro-5-H-dibenzo[a,d]cycloheptene was substituted for diphenylmethylchloride. (10,11-Dihydro-5H-dibenzo[1;d]cyclohepten-4-yl)phenylacetonitrile was obtained, having a melting point of 134.1–147.7° C.

EXAMPLE 4

2-(4-Chlorophenyl)-3,3-diphenylpropionitrile was made using the same procedure as described for Example 1, but substituting 4-chlorophenylacetonitrile for phenylacetonitrile. The compound obtained had a melting point of 115.1–115.6° C.

EXAMPLE 5

2-(2-Thienyl)-3,3-diphenylpropionitrile was made using the following procedure. To a mixture of 2-thiophenacetonitrile (16.30 g, 0.081 mol), benzyltriethylammonium chloride (0.185 g, 0.900081 mol), and 50% sodium hydroxide, diphenylmethylchloride (10.00 g, 0.081 mol) was added dropwise. this mixture was stirred for two hours at room temperature, heated at 40° C. for 30 minutes and then was treated with benzaldehyde (0,18 g, 0.0017 mol), The reaction mixture was poured into an ice-water mixture (200 ml) and extracted twice with dichloromethane. The organic layers were combined, washed with 2N hydrochloric acid (100 ml), water (100 ml), and saturated sodium chloride solution (100 ml), dried over magnesium sulfate, filtered and evaporated. The residue was chromatographed on flash silica to give a solid which was recrystallized three times from ethanol affording 17.45 g (74.3%) of 2-(2-Thienyl)-3,3-diphenylpropionitrile as a crystalline solid, having a melting point of 102.7–105.3° C.

EXAMPLE 6

3,3-Bis-(4-fluorophenyl)-2-phenylpropionitrile was made using the same procedure as described in Example 5, but substituting phenylacetonitrile for 2-thiophenacetonitrile and chlorobis(4-fluorophenyl)methane for diphenylmethylchloride. The end product had a melting point of 142.5–143.8° C.

EXAMPLE 7

2-4-Iodophenyl)-3,3-diphenylpropionitrile was made using the same procedure as described in Example 5, but substituting 4-iodophenylacetonitrile for 2-thiopheneacetonitrile.

EXAMPLE 8

1,2,2-Triphenylcyclopropylnitrile was made using the procedure of C. R.

Hauser, T. M. Harris, and T. G. Ledford [*J. Amer. Chem. Soc.*, 1959, 81, 4099–4102]. A solution of $KNH_2$ and liquid $NH_3$ was made by adding potassium (24.5 g, 0.63 mol) to liquid $NH_3$ (1500 ml). 2,3,3-triphenylpropionitrile (87.5 g, 0.31 mol) was slowly added to the $KNH_2/NH_3$ solution. After stirring for 10 minutes, this mixture was treated with a solution of dichloromethane (31.5 g, 0.37 mol) and diethyl ether (150 ml). After 1.5 hour, another portion of dichloromethane (6.0 g, 0.071 mol) and diethyl ether (25.0 ml) was added and the reaction mixture stirred for another hour at −78° C. Diethyl ether was added and the $NH_3$ was allowed to evaporate. The ethereal solution was washed with water, 2N hydrochloric acid and water. The organic layer was separated, dried over potassium carbonate, filtered and evaporated to a solid residue. This material was recrystallized twice from methanol affording 47.0 g (51%) of 1,2,2-Triphenylcyclopropylnitrile as a crystalline solid.

EXAMPLE 9

2,3,3-Tiphenylpropylamine was made according to the following procedure. A solution of 2,3,3-triphenylpropionitrile (10.00 g, 0.035 mol) and THF (80 ml) was added dropwise to a solution of $LiAlH_4$ (3.40 g, 0.089 mol) in THF (100 ml) at 0° C. The resulting mixture was stirred for 24 hours at room temperature and then refluxed for 24 hours. After cooling in an ice bath, the reaction mixture was treated with water (3.40 ml), 3N sodium hydroxide (10.20 ml) and water (3.4 ml) followed by the addition of magnesium sulfate. The mixture was filtered and the filtrate was evaporated to an oil. This material was dissolved in diethyl ether (30 ml) and diethyl ether/anhydrous hydrochloric acid (25 ml, 0.025 mol) was added. A white solid was filtered and partitioned between diethyl ether and 3N sodium hydroxide. The organic layer was separated, dried over potassium carbonate, filtered, and evaporated affording 2,3,3-Tiphenylpropylamine as a crystalline solid.

EXAMPLE 10

2-(4-Chlorophenyl)-3,3-diphenylpropylamine was made using the same procedure as described in Example 9, but substituting 2-4-(Chlorophenyl)-3,3-diphenylpropionitrile for 2,3,3-triphenylpropionitrile. The end product had a melting point of 104.1–105.7° C.

EXAMPLE 11

2-(9H-[Fluoren-9-yl])-2-(phenyl)ethylamine was made using the procedure as set forth in Example 9, but substituting 9H-(Fluoren-9-yl)phenylacetonitrile or 2,3,3-triphenylpropionitrile and diethyl ether for THF. An oil was obtained.

EXAMPLE 12

3,3-Bis-(4-fluorophenyl)-2-(phenyl)propylamine was made using the procedure as set forth in Example 9, but substituting 3,3-bis-(4-fluorophenyl)-2-phenylpropionitrile for 2,3,3-triphenylpropionitrile and diethyl ether for THF. The endproduct was a white solid.

EXAMPLE 13

3,3-Diphenyl-2-(2-thienyl)propylamine was made using the procedure as set forth in Example 9, but substituting 2-(2-Thienyl)-3,3-diphenylpropionitrile for 2,3,3-triphenylpropionitrile and diethyl ether for THF. The end product was a beige solid having a melting point greater than 200° C. (decomposition).

EXAMPLE 14

1,2,2-triphenylcydopropylmethylamine was made using the procedure as set forth in Example 9, but substituting 1,2,2-Triphenylcyclopropylnitrile for 2,3,3-triphenylpropionitrile and diethyl ether for THF. The end product was a white solid.

EXAMPLE 15

2-(4-lodophenyl)-3,3-diphenylpropylamine was made using the following procedure. A solution of TFA (3.30 g, 0.030 mol) and THF (10 ml) was slowly added to a slurry of sodium borohydrate (1.10 g, 0.029 mol) and THF (20 ml) at room temperature. After gas evolution ceased, the reaction was stirred for fifteen minutes and then treated dropwise with a solution of 2-(4-lodophenyl)-3,3-diphenylpropionitrile (4,87 g, 0.012 mol) and THF (20 ml). After stirring overnight at room temperature, water was added slowly followed by dichloromethane (40 ml). The organic layer was dried over potassium carbonate, filtered and evaporated to an oil. This material was dissolved in diethyl ether and treated with anhydrous hydrochloric acid/diethyl ether (10 ml). A white solid was filtered and partitioned between dichloromethane and 3N sodium hydroxide. The organic layer was separated, dried over potassium carbonate, filtered and evaporated to give 2-(4-lodophenyl)-3,3-diphenylpropylamine as a solid.

EXAMPLE 16

2-(10,11 -Dihydro-5H-dibenzo[11,d]cyclohepten4-yl)-2-(phenyl)ethylamine was made as follows. A solution of 1 M BH$_3$-THF (24 ml, 0.024 mol) at room temperature was treated with a solution of (10,11-Dihydro-5H-dibenzo[1,d]cyclohepten-4-yl)phenylacetonitrile (5.0 g, 0.016 mol) and THF (70 ml). The resulting solution was refluxed for 2 hours, cooled to 0° C. and treated with methanol (50 ml) followed by 6N hydrochloric acid (125 ml). The mixture was heated at 70° C. for 1 hour, cooled to 0° C., adjusted to pH 12 with 50% sodium hydroxide solution, and extracted two times with ethylacetate. The organic layers were combined, dried, filtered, and evaporated to a yellow oil. This material was triturated with hexane and filtered. The filtrate was evaporated and the residue was chromatographed on flash silica using ethylacetate:hexane (8:2) as the eluant to give a 2.29 9 (46%) yield of 2-(10,11-Dihydro-5H-dibenzo[1,d]cyclohepten)-2-(phenyl)ethylamine as an oil.

EXAMPLE 17

Compound 29 was made in accordance with the following procedure. A solution of thiopheneacetyl chloride (0.281 g, 0.0017 mol) and ethylene dichloride (8.0 ml) was added slowly to an ice led mixture of 2,3,3-Tiphenylpropylamine (0.50 g, 0.0017 mol), sodium acetate (0.18 g, 0.0022 mol) and ethylene chloride (8.0 ml). After stirring overnight at room temperature, water was added with thorough mixing. The resulting organic layer was separated, washed successively with 1 N sodium hydroxide solution and 1 N hydrochloric acid solution, dried over magnesium sulfate, filtered and evaporated to an oil which solidified. Two recrystallizations of this material afforded 0.410 g (59%) of 29 as a crystalline solid, having a melting point of 130–132° C.

EXAMPLE 18

Other compounds may be obtained in accordance with the procedure set forth in Example 17, requiring the substitution for thiopheneacetyl chloride or 2,3,3-Tiphenylpropylamine, such as compounds: 1, 6, 7, 18, 29, 78, 79, and 82.

EXAMPLE 19

Compound 80 was made using the following procedure: A solution of 2-chlorphenylacetic acid (0.289 g, 0.0017 mol), 1,1'-carbonyldiimidazole (0.271 g, 0.0017 mol) and acetonitrile (25 ml) was stirred for twenty minutes at room temperature and treated with 1,2,2-triphenylcydopropylmethylamine (0.500 g, 0.0017 mol). After stirring for 24 hours, the reaction was evaporated and the residue dissolved in methylene dichloride. This solution was washed with water (10 ml), 1 N HCl (10 ml), and water (10 ml). The organic layer was separated, dried over magnesium sulfate, filtered, and evaporated to an oil. This material was dissolved in ethylene dichloride and diethyl ether was added causing a crystalline solid to form. Filtration afforded 0.501 g (65%) of 80 as a crystalline solid with a melting point of 128.5–130.5° C.

EXAMPLE 20

Following the procedure of Example 19, substituting for the 2-chlorophenylacetic acid or 1,2,2-triphenylcydopropylmethylamine equivalent amounts of the appropriate starting materials and substituting ethylene dichloride for the acetonitrile used therein, the following compounds may be obtained: 2, 3, 4, 5, 8, 9, 10, 11, 12, 13, 14, 19, 20, 21, 22, 24, 25, 26, 27, 28, 30, 34, 37, 38, 39, 40, 41, 42, 43,45, 46, 48, 49, 61, 62, 63, 64, 81, 83, 84, 85, 86, 87, 88, 89, and 90.

EXAMPLE 21

Compound 66 was made as follows: A solution of phenyl acetic acid (0.30 g, 0.0024 mol), 2-(9H-[Fluoren-9-yl])-2-(phenyl)ethylamine (0.70 g, 0.0024 mol), and ethylene dichloride (10 ml) was treated with 1-(3-dimethylaminopropyl)-3-ethylcarondiimide hydrochloride (0.55 g, 0.0029 mol). After stirring overnight, the reaction solution was washed with 3 N sodium hydroxide, 6 N HCl and saturated NaCl solution. The organic layer was separated, deed over magnesium sulfate and evaporated to a semi-solid. This material was triturated with diethyl ether and filtered to give a solid which was recrystallized from methanol affording 0.12 g (12%) of Compound 66 as a white crystalline solid having a melting point of 148.7–150.8° C.

EXAMPLE 22

Following the procedure of Example 21, substituting for the phenylacetic acid or 2-(9H-[Fluoren-9-yl])-2-(phenyl)ethylamine equivalent amounts of the appropriate starting materials, the following compounds may be obtained: 15, 16, 17, 23,31, 32, 44, 65, 67,68, 69, 70, 71, 72, 74, 75, 76, 77, and 91.

EXAMPLE 23

Compound 52 was made in accordance with the following procedure: A solution of 2,3,3-Tiphenylpropylamine (0.25 g, 0.0009 mol) and methylene dichloride (25 ml) was treated with 2-chlorophenyl isocyanate (0.13 g, 0.0009 mol) at room temperature. A solid formed which was filtered and recrystallized from methanol-hexane to give 0.14 g (75%) of 52 as a white crystalline solid having a melting point of 210–211° C.

EXAMPLE 24

Following the procedure of Example 23, substituting for the chlorophenyl isocyanate or 2,3,3-Tiphenylpropylamine used therein, equivalent amounts of the appropriate starting materials, the following compounds may be obtained: 50, 51, 53,54, 55, 92, 93, 94, and 95

EXAMPLE 25

Compound 40 was made as follows: An ice-cooled solution of 2,3,3-tiphenylpropylamine (0.674 g, 0.0024 mol) and $CHCl_3$ (20 ml) was treated with 2-thiophenesutfonyl chloride (0.475 g, 0.0026 mol) followed by diisopropylethylamine (0.764 g, 0.0059 mol) and stirred at room temperature overnight. The reaction was washed with 1 N HCI (20 ml) and saturated NaCl solution. The organic layer was separated, dried over magnesium sulfate, filtered and evaporated affording 0.660 g (66%) of 40 as a solid having a melting point of 169–170.9° C.

EXAMPLE 26

Following the procedure of Example 25, substituting for the 2,3,3-Tiphenylpropylamine used therein an equivalent amount of 2-(4-chlorophenyl)-3,3-diphenylpropylamine, compound 41 may be obtained.

EXAMPLE 27

Compound 57 was made in accordance with the following procedure: To a solution of 2,3,3-Tiphenylpropylamine (0.25 g, 00009 mol), triethylamine (0.09 g, 0.0009 mol) and $CHCl_3$ (25 ml) was added 4-fluorophenyl chloroformate (0.2 g, 0.0009 mol) and the resulting solution was stirred for 45 minutes. The reaction was then washed with 1 N HCI, and brine. The organic layer was separated, dried over magnesium sulfate, filtered and evaporated to white solid. This material was recrystallized form methanol/hexane to give 0.15 g (39%) of 57 as a white crystalline solid having a melting point of 150–151° C.

EXAMPLE 28

Following the procedure of Example 27, but substituting for the 2,3,3-Triphenylpropylamine and 4-fluorophenyl chloroformate used therein, equivalent amounts of the appropriate starting materials, the following compounds may be obtained: 56, 58, 59, 96, and 97.

EXAMPLE 29

Compound 17 was made as follows: A mixture of N-[3,3-bis-(4-fluorophenyl)-2-phenylpropyl]-2-phenylacetamide [Compound 18] (0.84 g, 0.0019 mol), dimethylsulfate (0.37 g, 0.0029 mol), benzyltriethylammonium chloride (0.14 g, 0.00075 mol), 50% NaOH (30 ml) was stirred overnight at room temperature. Water was added and the mixture was extracted with ethylene dichloride. The organic layer was separated, dried over potassium carbonate, filtered and evaporated to an oil which was crystallized from diethyl ether-hexane affording 0.080 g (9%) of 17 as a yellow crystalline solid having a melting point of 86.9–88.2° C.

EXAMPLE 30

Compound 98 was prepared as follows: A mixture of 2-(3,4-methylenedioxyphenyl)-3,3-diphenylpropylamine (18.0 g, 0.055 mol) and anhydrous THF (120 mL) at –70° C. was treated dropwise with a 1.0M solution of DiBAL (100 mL, 0.110 mol). The reaction was stirred for 1 hour at –70° C. and then at 25° C. for 1.5 hours. The reaction was cooled to 0° C. and treated with ethanol (20 mL) followed by 10% aqueous HCl (150 mL). Extraction with ethyl acetate, drying over anhydrous $MgSO_4$, evaporation and purification by flash chromatography (silica gel) afforded 2-(3,4-methylenedioxyphenyl)-3,3-diphenylpropionaldehyde a solid. A mixture of this material (8.0 g, 0.024 mol), Rink amine resin (8.73 g, 0.0044 mol), and trimethylorthoformate (60 mL) was shaken for 4 days, filtered and washed twice with trimethylorthoformate, methylene chloride, and dichoroethane. The resulting resin was shaken with $NaBH(Oac)_3$ (4.63 g, 0.022 mol), acetic acid (1.83 mL) and dichloromethane (60 mL) for two days. The resulting resin was washed with methanol, methylene chloride, 10% acetic acid/methylene chloride, 10% triethylamine/methylene chloride, methylene chloride, and methanol. This resin (0.235 g, 0.0001 mol) was shaken for 2 days with HATU (0.090 g, 0.00024 mol), diisopropylethylamine, (175 µL), 4-chlorophenylacetic acid (0.085 g, 0.0005 mol), and DMF (2 mL). The resin was filtered and washed three times each with DMF, methylene chloride, and methanol and dried. The dried resin was treated with 10% TFA/methylene chloride and filtered. The filtrate was blown dry with nitrogen to afford 0.042 g (87%) of compound 98, electrospray mass spectrometry m/e=484.

EXAMPLE 31

Following the procedure of Example 30, but substituting for the 4-chlorophenylacetic acid and 2-(3,4-methylenedioxyphenyl)-3,3-diphenylpropylamine used therein, equivalent amounts of the appropriate starting materials, the following compounds may be obtained: 99–161, 164, 168, 173,174, 176–178, 180, and 182.

EXAMPLE 32

Compound 162 was prepared as follows: A solution of 1-(3-dimethylaminopropyl)-3-ethylcarbodiimide hydrochloride (7.67 g, 0.040 mol) and methylene chloride (300 mL) was washed with 10% $NH_4OH$, dried over $MgSO_4$, filtered and evaporated. The residue was dissolved in DMF (100 mL) and mixed with Merrifield resin (20.0 g, 0.020 mol) at 100° C. overnight. The mixture was filtered and the resin was washed with DMF, methanol, and methylene chloride. A mixture of this resin (0.48 g, 0.00048 mol), 4-chlorophenylacetic acid (0.0205 g, 0.00012 mol), 2(4-iodophenyl)-3,3-diphenylpropylamine (0.0413 g, 0.0001 mol), and $CHCl_3$ (20 mL) was agitated for 2 days, filtered, and washed with $CHCl_3$. The filtrate was blown dry with nitrogen affording compound 163, 0.0425g. (88%), Cl mass spectrometry m/e=483.99.

EXAMPLE 33

Following the procedure of Example 32, but substituting for the 4-chlorophenylacetic acid used therein, equivalent amounts of the appropriate starting materials, the following compounds may be obtained: 163, 165–167, 169–172, 175, 179, 181, and 183.

EXAMPLE 34

A human glucocorticoid receptor binding assay was carried out to determine the extent to which the compounds of this invention have the ability to bind to human glucocorticoid receptors. This binding ability may be indicative of the antiinflammatory activity of the compound. The test was carried out as follows.

Human glucocorticoid receptors were prepared from either insect cells (Sf21) infected with baculovirus hGR or from a lymphoblast cell line which expresses high levels of endogenous hGR (IM9). The receptor binding reactions, with or without test compounds, were set up in 96-well microtiter plates which were previously siliconized with SIGMACOTE™, a chlorinated organopolysiloxane in heptane. The binding components, 3(H) Triamcinolone acetonide (TAA), glycerol/molybdate-containing buffer and unlabeled compounds were added to the wells using a combination of BIOMEK laboratory automation system and repeat pipettes. After four hours of incubation, the samples were precipitated with polyethylene glycol and filtered through Whatman GF/F paper using a TOMTEK cell harvester. The filter mate with 96 samples were bound to a solid-phase scintillant and directly counted in a BETAPLATE counter. The $IC_{50}$ values were determined based on competition of $^3$H TAA with the test compounds at 6–8 concentrations ranging from $10^{-10}$–$10^{-5}$ M and calculated using the Chung-Prusoff equation. The activity of test compounds to displace 3(H) TAA binding to hGR is also expressed as percent inhibition at 1 $\mu$M. The results of this test are set forth in Table 1 below.

EXAMPLE 35

A human progesterone receptor binding assay was performed in order to determine selectivity of the compounds, as follows. Human progesterone receptors were prepared from either insect cells (SF21) infected with baculovirus hPR A, or from a breast cancer cell line, T47D, which expresses high levels of endogenous hPR. The receptor binding reactions, with or without test compounds, were set up in 96-well microtiter plates which were previously siliconized with SIGMACOTE. The binding components, 3(H) R5020 Promegestone, a high affinity ligand for the progesterone receptors, glycerol/molybdate-containing buffer and unlabeled compounds were added to the wells using a combination of BIOMEK laboratory automation system and repeat pipettes. After overnight incubation, the samples were precipitated with polyethylene glycol and filtered through Whatman GF/F paper using a TOMTEK cell harvester. The filter mate with 96 samples were bound to a solid-phase scintillant and directly counted in the BETAPLATE counter. Only those compounds that were active in the human glucocorticoid receptor assay set forth in Example 30 were used for progesterone receptor binding to determine cross-reactivity profiles, if any. The activity of test compounds to displace 3(H) R5020 binding to hPR is expressed as percent inhibition at the two concentrations, $10^{-6}$ and $10^{-5}$ Molar. Those compounds that do not inhibit 3(H) TAA binding by 50% at $10^{-5}$ M were not considered active. Surprisingly, the compounds of this invention selectively binds to the hGR but show little or no affinity for the hPR.

EXAMPLE 36

Several triphenylpropanamide compounds of this invention, having varying affinities for the human glucocorticoid receptor, were tested for topical antiinflammatory activity in mouse ear inflammation models. Compounds with low receptor affinity ($IC_{50}$>20 nM) were weakly active or inactive at reducing ear inflammation induced by the contact sensitizer oxazolone. Compounds having receptor affinities closer to hydrocortisone were as nearly active as hydrocortisone in suppressing mouse oxazolone-induced contact hypersensitization (MOCH) and phorbol ester-induced ear edema. The in vivo studies of this example were conducted as follows.

Albino male CD1 mice, 7–9 weeks old were used in this example. A 0.005% (w/v) TPA or 20% (w/v) arachidonic acid (AA) solution was made in acetone. A 20 $\mu$l volume of the TPA or AA was applied to the dorsal left ear of the mouse. Compounds of this invention were placed in a composition containing ethanol/propylene glycol at a ratio of 70:30 were applied to the left ear of each mouse in an amount of 20 $\mu$l immediately after application of the TPA or AA. The right ear was not treated. The mice were sacrificed by carbon dioxide inhalation 5.5 hours after administration of TPA and one hour after administration of AA, the left and right ears were removed and a 7 mm biopsy was removed from each ear and weighed. The difference in biopsy weights between the right and left ears was calculated. Antiinflammatory effects of compounds were evident as an inhibition of the increase in ear weight.

In determining the MOCH using the compounds of this invention, albino male CD-1 mice, 7–9 weeks old were induced on the shaved abdomen with 50 $\mu$l of 3% oxazolone in acetone/corn oil (Day 0). On Day 5, a 20 $\mu$l volume of 2% oxazolone in acetone was applied to the dorsal left ear of the mouse. Compounds (made in ethanol/propylene glycol, 70:30) were applied to the left ear in 20 $\mu$l volume, one hour after oxazolone challenge. The right ear was not treated. The mice were sacrificed by carbon dioxide inhalation 24 hours after oxazolone challenge, the left and right ears were removed and a 7 mm biopsy was removed from each ear and weighed. The difference in biopsy weights between the right and left ears was calculated. Antiinflammatory effects of compounds were evident as an inhibition of the increase in ear weight.

The result of the foregoing in vivo testing is set forth in the following Table 2:

TABLE 2

| Compound No. | Oxazolone Ear Swelling (MOCH) % inhibition vs. Vehicle at 1 mg |
|---|---|
| 2 | 4 |
| 4 | 1 |
| 5 | 13 |
| 6 | 38 |
| 9 | 18 |
| 10 | 19 |
| 11 | 33 |
| 12 | 36 |
| 13 | 10 |
| 14 | 11 |
| 15 | 47 |
| 16 | 46 |
| 19 | 2 |
| 20 | 32 |
| 22 | 15 |
| 23 | 41 |
| 24 | 21 |
| 25 | 9 |
| 26 | −5 |
| 27 | 20 |
| 28 | 28 |
| 29 | 83 |
| 30 | 21 |
| 31 | 14 |
| 32 | 83 |
| 33 | 74 |
| 34 | 29 |
| 35 | 36 |
| 36 | 13 |
| 37 | 25 |
| 38 | 13 |
| 39 | 24 |
| 40 | 15 |
| 41 | 3 |

TABLE 2-continued

| Compound No. | Oxazolone Ear Swelling (MOCH) % inhibition vs. Vehicle at 1 mg |
|---|---|
| 42 | 27 |
| 43 | 47 |
| 44 | 3 |
| 45 | 31 |
| 46 | 4 |
| 47 | 51 |
| 48 | 22 |
| 49 | 20 |
| 50 | 30 |
| 53 | 24 |
| 54 | 10 |
| 55 | 18 |
| 56 | 38 |
| 57 | 13 |
| 58 | 16 |
| 60 | 27 |
| 61 | 17 |
| 62 | 36 |
| 63 | 3 |
| 64 | 26 |
| 65 | 13 |
| 66 | 20 |
| 68 | 28 |
| 69 | 43 |
| 72 | 50 |
| 74 | 18 |
| 75 | 26 |
| 76 | 23 |
| 77 | 41 |
| 79 | 18 |
| 80 | 54 |
| 81 | 22 |
| 82 | 23 |
| 83 | −4 |
| 84 | 54 |
| 85 | 16 |
| 87 | 22 |
| 88 | 29 |
| 89 | 16 |
| 90 | 65 |
| 91 | 13 |
| 92 | 42 |
| 93 | 26 |
| 94 | 35 |
| 95 | 16 |
| 96 | 52 |
| 97 | 50 |
| 98 | 85 |
| hydrocortisone | 75–85 |

In accordance with the foregoing table, for example, compounds 23, 15, and 16 had moderate topical activity whereas compounds 29, 32, and 98 were equiactive with hydrocortisone. Compounds 29 and 32 were tested for dose-related activity in the oxazolone model. As shown below in Table 3, both compounds inhibited ear swelling in a dose-dependent manner.

TABLE 3

| Treatment | Dose (%) | Oxazolone Ear swelling % Inhibition vs. Vehicle | |
|---|---|---|---|
| | | Experiment 1 | Experiment 2 |
| Hydrocortisone | 1 | 78.9 | 58.2 |
| Compound 29 | 3 | 66.5 | — |
| | 1 | 49.9 | — |
| | 0.3 | 34.7 | — |
| | 0.1 | 4.3 | — |
| Compound 32 | 3 | — | 36.5 |
| | 1 | — | 31.45 |

TABLE 3-continued

| Treatment | Dose (%) | Oxazolone Ear swelling % Inhibition vs. Vehicle | |
|---|---|---|---|
| | | Experiment 1 | Experiment 2 |
| | 0.3 | — | 18.95 |
| | 0.1 | — | 11.2 |

Both compounds were also tested in a TPA-induced ear edema model, which also shows effect of glucocorticoids. At equivalent doses, the two non-steroidal compounds were only slightly less active than hydrocortisone, as set forth in Table 4 below.

TABLE 4

| Treatment | Dose (%) | % Inhibition of TPA Ear Edema vs. Vehicle |
|---|---|---|
| Hydrocortisone | 1 | 80.6 |
| Compound 29 | 1 | 64.9 |
| Compound 32 | 1 | 60.0 |

These tests demonstrate that the compounds of this invention (triphenylpropanamides) are topically active as antiinflammatory agents. Because of their selective effects on transcription factors, they should not cause the side effects known to be associated with classical glucocorticoids. In addition to inflammation, the triphenylpropanamides of this invention may be useful as therapeutics in other glucocorticoid-responsive skin conditions.

What is claimed is:

1. A compound having the formula:

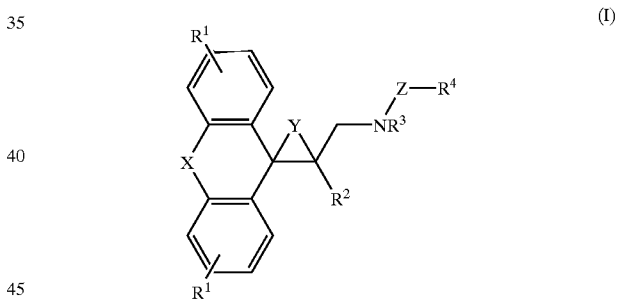

(I)

wherein X is selected from the group consisting of a single bond, $(CH_2)_n$ wherein n is an integer from 1 to 3 and —HC=CH—;

$R^1$ is hydrogen or is from one to three substituent groups each selected from the group consisting of lower alkyl $(C_2–C_6)$, lower alkoxy, hydroxy, halo, carboxy, carboalkoxy, amino, amido, sulfonamido or nitrile;

$R^2$ is a phenyl group in which said phenyl group is substituted with hydrogen or from one to three substituent groups each selected from the group consisting of lower alkyl($C_2–C_6$), lower alkoxy, lower alkylenoxy, hydroxy, halo, carboxy, carboalkoxy, amino, amido, sulfonamido or nitrile, a heteroaromatic ring selected from the group consisting of substituted- and unsubstituted thiophene, furan, pyrrole, or pyridine;

Y is selected from the group consisting of —CH$_2$— and H, H;

$R^3$ is selected from the group consisting of hydrogen; alkyl; cycloalkyl; alkenyl; alkynyl; phenyl in which said phenyl group is substituted with hydrogen or from one to three substituent groups each selected from the group consisting of lower alkyl, lower alkoxy, hydroxy, halo, carboxy, carboalkoxy, amino, amido, sulfonamido or nitrile; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido and nitrile;

Z is selected from the group consisting of carbonyl; carboxy; carbonylamino; or sulfone; and $R^4$ is phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido and nitrile; a heteroaromatic ring selected from the group consisting of substituted- or unsubstituted thiophene, benzothiophene, furan, pyrrole, pyridine, and a heteroaromatic ring connected by a lower alkyl chain wherein said heteroaromatic ring is selected from the group consisting of substituted- or unsubstituted thiophene, furan, pyrrole and pyridine; and $R^5$ is selected from the group consisting of: hydrogen; alkyl; cycloalkyl; alkenyl; alkynyl; phenyl, in which said phenyl group is substituted with hydrogen or from one to three substituent groups each selected from the group consisting of lower alkyl ($C_2$–$C_6$), lower alkoxy, hydroxy, halo, carboxy, carboalkoxy, amino, amido, sulfonamido, and nitrile; phenyl lower alkyl in which said phenyl group is substituted with hydrogen or with from one to three substituent groups each selected from the group consisting of lower alkyl, lower alkoxy, hydroxy, halo, carboxy, carboalkoxy, amino, amido, sulfonamido and nitrile.

2. A compound according to claim 1 wherein $R^1$ is selected from the group consisting of hydrogen and halogen.

3. A compound according to claim 2 wherein $R^1$ is hydrogen.

4. A compound according to claim 2 wherein $R^1$ is halogen.

5. A compound according to claim 4 wherein $R^1$ is fluorine.

6. A compound according to claim 1 wherein $R^2$ is selected from the group consisting of phenyl and halophenyl.

7. A compound according to claim 6 wherein $R^2$ is phenyl.

8. A compound according to claim 6 wherein $R^2$ is halophenyl.

9. A compound according to claim 8 wherein $R^2$ is chlorophenyl.

10. A compound according to claim 1 wherein $R^3$ is selected from the group consisting of hydrogen and lower alkyl.

11. A compound according to claim 10 wherein $R^3$ is hydrogen.

12. A compound according to claim 1 wherein $R^4$ is heteroaromatic lower alkyl.

13. A compound according to claim 12 wherein $R^4$ is thiophene.

14. compound according to claim 1 wherein Z is carbonyl.

15. An antiinflammatory composition comprising a pharmaceutically acceptable carrier and an antiinflammatory-effective amount of a compound having the formula:

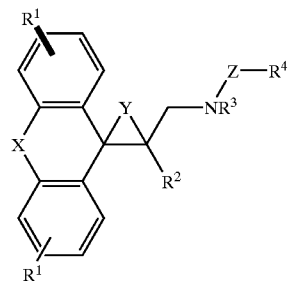

(I)

wherein X is selected from the group consisting of a single bond, $(CH_2)_n$ wherein n is an integer from 1 to 3 and —HC=CH—;

$R^1$ is hydrogen or is from one to three substituent groups each selected from the group consisting of lower alkyl ($C_2$–$C_6$), lower alkoxy, hydroxy, halo, carboxy, carboalkoxy, amino, amido, sulfonamido and nitrile;

$R^2$ is a phenyl group in which said phenyl group is substituted with hydrogen or from one to three substituent groups each selected from the group consisting of lower alkyl($C_2$–$C_6$), lower alkoxy, lower alkylenoxy, hydroxy, halo, carboxy, carboalkoxy, amino, amido, sulfonamido or nitrile, a heteroaromatic ring selected from the group consisting of substituted- or unsubstituted thiophene, furan, pyrrole, and pyridine;

Y is selected from the group consisting of —$CH_2$— and H, H;

$R^3$ is chosen from the group consisting of hydrogen; alkyl; cycloalkyl; alkenyl; alkynyl; phenyl in which said phenyl group is substituted with hydrogen or from one to three substituent groups each selected from the group consisting of lower alkyl, lower alkoxy, hydroxy, halo, carboxy, carboalkoxy, amino, amido, sulfonamido and nitrile; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido and nitrile;

Z is selected from the group consisting of carbonyl; carboxy; carbonylamino; and sulfone; and $R^4$ is straight- or branched-chain alkyl having from 2 to 12 carbon atoms; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido and nitrile; a heteroaromatic ring selected from the group consisting of substituted- or unsubstituted thiophene, furan, pyrrole, pyridine, and a heteroaromatic ring connected by a lower alkyl chain wherein said heteroaromatic ring is selected from the group consisting of substituted- or unsubstituted thiophene, furan, pyrrole and pyridine; and $R^5$ is selected from the group consisting of: hydrogen; alkyl; cycloalkyl; alkenyl; alkynyl; phenyl, in which said phenyl group is substituted with hydrogen or from one to three substituent groups each selected from the group consisting of lower alkyl ($C_2$–$C_6$), lower alkoxy, hydroxy, halo, carboxy, carboalkoxy, amino, amido, sulfonamido, and nitrile; phenyl lower alkyl in which said phenyl group is substituted with hydrogen or with from one to three substituent groups each selected from the group consisting of lower alkyl, lower alkoxy, hydroxy, halo, carboxy, carboalkoxy, amino, amido, sulfonamido and nitrile.

16. A composition according to claim 15 wherein $R^1$ is selected from the group consisting of hydrogen and halogen.

17. A composition according to claim 16 wherein $R^1$ is hydrogen.

18. A composition according to claim 16 wherein $R^1$ is halogen.

19. A composition according to claim 18 wherein $R^1$ is fluorine.

20. A composition according to claim 15 wherein $R^2$ is selected from the group consisting of phenyl and halophenyl.

21. A composition according to claim 20 wherein $R^2$ is phenyl.

22. A composition according to claim 20 wherein $R^2$ is halophenyl.

23. A composition according to claim 22 wherein $R^2$ is chlorophenyl.

24. A composition according to claim 15 wherein $R^3$ is selected from the group consisting of hydrogen and lower alkyl.

25. A composition according to claim 24 wherein $R^3$ is hydrogen.

26. A composition according to claim 15 wherein $R^4$ is heteroaromatic lower alkyl.

27. A composition according to claim 26 wherein $R^4$ is thiophene.

28. A composition according to claim 15 wherein Z is carbonyl.

29. A method of making a compound having the formula:

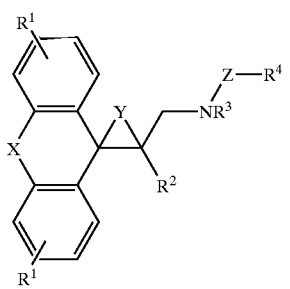

(I)

wherein X is selected from the group consisting of a single bond, $(CH_2)_n$ wherein n is an integer from 1 to 3 and —HC=CH—;

$R^1$ is hydrogen or is from one to three substituent groups each selected from the group consisting of lower alkyl ($C_2$–$C_6$), lower alkoxy, hydroxy, halo, carboxy, carboalkoxy, amino, amido, sulfonamido or nitrile;

$R^2$ is a phenyl group in which said phenyl group is substituted with hydrogen or from one to three substituent groups each selected from the group consisting of lower alkyl($C_2$–$C_6$), lower alkoxy, hydroxy, halo, carboxy, carboalkoxy, amino, amido, sulfonamido or nitrile, a heteroaromatic ring selected from the group consisting of substituted- or unsubstituted thiophene, furan, pyrrole, or pyridine;

Y is H, H;

$R^3$ is chosen from the group consisting of hydrogen; alkyl; cycloalkyl; alkenyl; alkynyl; phenyl in which said phenyl group is substituted with hydrogen or from one to three substituent groups each selected from the group consisting of lower alkyl, lower alkoxy, hydroxy, halo, carboxy, carboalkoxy, amino, amido, sulfonamido or nitrile; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido and nitrite;

Z is selected from the group consisting of carbonyl; carboxy; carbonylamino; and sulfone; and $R^4$ is straight- or branched-chain alkyl having from 2 to 12 carbon atoms; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido or nitrile; a heteroaromatic ring selected from the group consisting of substituted- or unsubstituted thiophene, furan, pyrrole, pyridine, or a heteroaromatic ring connected by a lower alkyl chain wherein said heteroaromatic ring is selected from the group consisting of substituted- or unsubstituted thiophene, furan, pyrrole and pyridine; and $R^5$ is selected from the group consisting of: hydrogen; alkyl; cydoalkyl; alkenyl; alkynyl; phenyl, in which said phenyl group is substituted with hydrogen or from one to three substituent groups each selected from the group consisting of lower alkyl ($C_2$–$C_6$), lower alkoxy, hydroxy, halo, carboxy, carboalkoxy, amino, amido, sulfonamido, and nitrile; phenyl lower alkyl in which said phenyl group is substituted with hydrogen or with from one to three substituent groups each selected from the group consisting of lower alkyl, lower alkoxy, hydroxy, halo, carboxy, carboalkoxy, amino, amido, sulfonamido and nitrile;

comprising the steps of (1) reacting $R^2CH_2CN$ with a compound having the formula (II) in the presence of n-butyl lithium:

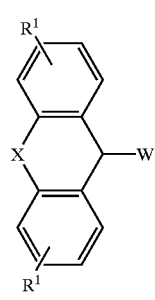

(II)

W = Cl, Br to obtain a compound having the formula (III)

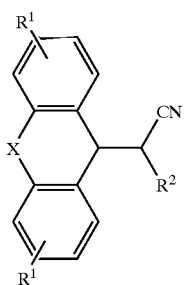

(2) reacting said compound of formula (III) with lithium aluminum hydride to form a compound of formula (IV):

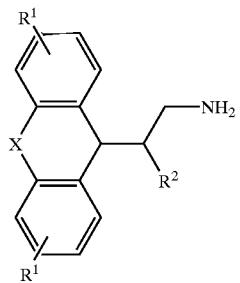

and (3) reacting said compound of formula (IV) with compound selected from the group consisting of: (a) sodium acetate and R⁴COCl; (b) CDI and R⁴CO₂H; (c) EtN=C=N(CH₂)₃ NMe₂HCl and R⁴CO₂H; and (d) ClCO₂R⁴; (e) ClC=O(NHR⁴); and (f) R⁴SO₂Cl to obtain a compound of formula (I).

30. A method of making a compound having the formula:

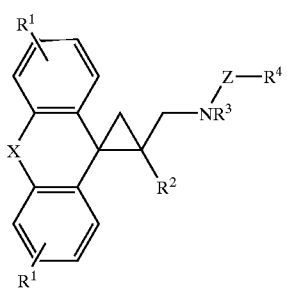

wherein X is selected from the group consisting of a single bond, (CH₂)ₙ wherein n is an integer from 1 to 3 and —HC=CH—;

R¹ is hydrogen or is from one to three substituent groups each selected from the group consisting of lower alkyl (C₂–C₆), lower alkoxy, hydroxy, halo, carboxy, carboalkoxy, amino, amido, sulfonamido and nitrile;

R² is a phenyl group in which said phenyl group is substituted with hydrogen or from one to three substituent groups each selected from the group consisting of lower alkyl(C₂–C₆), lower alkoxy, lower alkylenoxy, hydroxy, halo, carboxy, carboalkoxy, amino, amido, sulfonamido and nitrile, a heteroaromatic ring selected from the group consisting of substituted- or unsubstituted thiophene, furan, pyrrole, and pyridine;

R³ is chosen from the group consisting of hydrogen; alkyl; cycloalkyl; alkenyl; alkynyl; phenyl in which said phenyl group is substituted with hydrogen or from one to three substituent groups each selected from the group consisting of lower alkyl, lower alkoxy, hydroxy, halo, carboxy, carboalkoxy, amino, amido, sulfonamido and nitrile; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido and nitrile;

Z is selected from the group consisting of carbonyl; carboxy; carbonylamino; or sulfone; and R⁴ is straight- or branched-chain alkyl having from 2 to 12 carbon atoms; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido or nitrile; a heteroaromatic ring selected from the group consisting of substituted- or unsubstituted thiophene, furan, pyrrole, pyridine, or a heteroaromatic ring connected by a lower alkyl chain wherein said heteroaromatic ring is chosen from substituted- or unsubstituted thiophene, furan, pyrrole and pyridine; and R⁵ is selected from the group consisting of: hydrogen; alkyl; cycloalkyl; alkenyl; alkynyl; phenyl, in which said phenyl group is substituted with hydrogen or from one to three substituent groups each selected from the group consisting of lower alkyl (C₂–C₆), lower alkoxy, hydroxy, halo, carboxy, carboalkoxy, amino, amido, sulfonamido, or nitrile; phenyl lower alkyl in which said phenyl group is substituted with hydrogen or with from one to three substituent groups each selected from the group consisting of lower alkyl, lower alkoxy, hydroxy, halo, carboxy, carboalkoxy, amino, amido, sulfonamido and nitrile;

comprising the steps of:

(1) reacting R²CH₂CN with a compound having the formula (II) in the presence of n-butyl lithium:

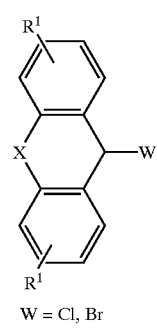

W = Cl, Br to obtain a compound having the formula (III)

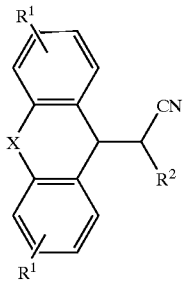

(III)

(2) reacting said compound of formula (III) with $CH_2Cl_2$ in the presence of $KNH_2$ and liquid $NH_3$ to obtain a compound having formula (V):

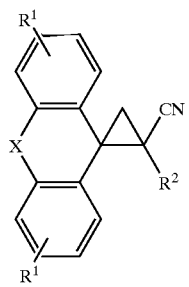

(V)

(3) reacting said compound of formula (V) with lithium aluminum hydride to form a compound of formula (VI):

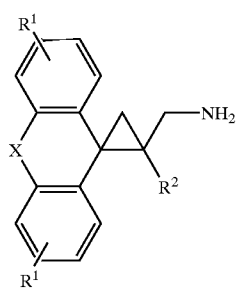

(VI)

and (4) reacting said compound of formula (VI) with compound selected from the group consisting of: (a) sodium acetate and $R^4COCl$; (b) CDl and $R^4CO_2H$; (c) $EtN=C=N(CH_2)3$ NMe2HCl and $R^4CO_2H$; (d) $ClCO_2R^4$; (e) $ClC=O(NHR^4)$; and (f) $R^4SO_2Cl$ to obtain a compound of formula (I).

31. A method of making a compound having the formula:

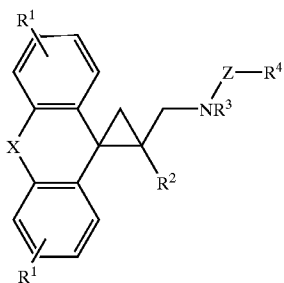

(I)

wherein X is selected from the group consisting of a single bond, $(CH_2)_n$ wherein n is an integer from 1 to 3 and —HC═CH—;

$R^1$ is hydrogen or is from one to three substituent groups each selected from the group consisting of lower alkyl $(C_2-C_6)$, lower alkoxy, hydroxy, halo, carboxy, carboalkoxy, amino, amido, sulfonamido or nitrile;

$R^2$ is a phenyl group in which said phenyl group is substituted with hydrogen or from one to three substituent groups each selected from the group consisting of lower alkyl$(C_2-C_6)$, lower alkoxy, lower alkylenoxy, hydroxy, halo, carboxy, carboalkoxy, amino, amido, sulfonamido or nitrile, a heteroaromatic ring selected from the group consisting of substituted- or unsubstituted thiophene, furan, pyrrole, and pyridine;

Y is selected from the group consisting of —CH$_2$— and H, H;

$R^3$ is hydrogen;

Z is selected from the group consisting of carbonyl; carboxy; carbonylamino; and sulfone; and $R^4$ is straight- or branched-chain alkyl having from 2 to 12 carbon atoms; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido or nitrile; a heteroaromatic ring selected from the group consisting of substituted- or unsubstituted thiophene, furan, pyrrole, pyridine, or a heteroaromatic ring connected by a lower alkyl chain wherein said heteroaromatic ring is chosen from substituted- or unsubstituted thiophene, furan, pyrrole and pyridine; and $R^5$ is selected from the group consisting of: hydrogen; alkyl; cycloalkyl; alkenyl; alkynyl; phenyl, in which said phenyl group is substituted with hydrogen or from one to three substituent groups each selected from the group consisting of lower alkyl $(C_2-C_6)$, lower alkoxy, hydroxy, halo, carboxy, carboalkoxy, amino, amido, sulfonamido, and nitrile; phenyl lower alkyl in which said phenyl group is substituted with hydrogen or with from one to three substituent groups each selected from the group consisting of lower alkyl, lower alkoxy, hydroxy, halo, carboxy, carboalkoxy, amino, amido, sulfonamido and nitrile;

comprising the steps of (1) reacting diisobutylaluminum hydride with a compound having the formula (VII):

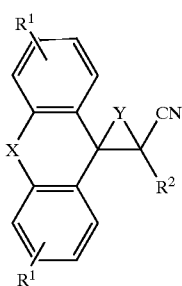

(VII)

to obtain a compound having the formula (VIII)

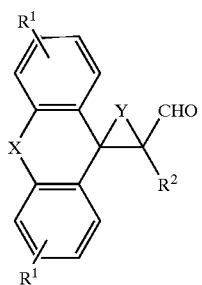

(VIII)

(2) reacting said compound of formula (VIII) with Rink resin to give a resin-bound compound of formula (IX):

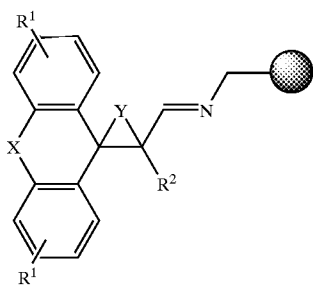

(IX)

(3) reacting said compound of formula (IX) with sodium triacetoxyborohydride to form a compound of formula (X):

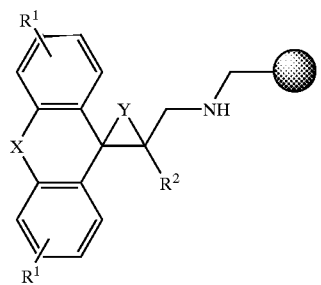

(X)

(4) reacting said compound of formula (X) with $R^4CO_2H$ in the presence of O—(7-azabenzotriazol-1-yl)-N,N,N', N'-tetramethyluronium hexafluorophasphate and diisopropyl ethylamine followed by treatment with TFA to form a compound of formula (I).

32. A method of making a compound having the formula:

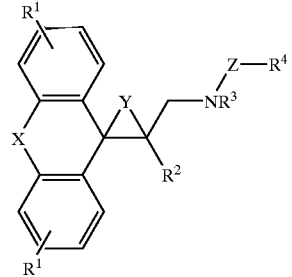

(I)

wherein X is selected from the group consisting of a single bond, $(CH_2)_n$ wherein n is an integer from 1 to 3 and —HC=CH—;

$R^1$ is hydrogen or is from one to three substituent groups each selected from the group consisting of lower alkyl $(C_2-C_6)$, lower alkoxy, hydroxy, halo, carboxy, carboalkoxy, amino, amido, sulfonamido and nitrile;

$R^2$ is a phenyl group in which said phenyl group is substituted with hydrogen or from one to three substituent groups each selected from the group consisting of lower alkyl$(C_2-C_6)$, lower alkoxy, lower alkylenoxy, hydroxy, halo, carboxy, carboalkoxy, amino, amido, sulfonamido or nitrile, a heteroaromatic ring selected from the group consisting of substituted- or unsubstituted thiophene, furan, pyrrole, or pyridine;

wherein Y is selected from the group consisting of —$CH_2$— and H, H;

$R^3$ is hydrogen;

Z is selected from the group consisting of carbonyl; carboxy; carbonylamino; and sulfone; and $R^4$ is straight- or branched-chain alkyl having from 2 to 12 carbon atoms; phenylloweralkyl in which said phenyl group is substituted with hydrogen or with one to three substituent groups each selected from the group consisting of lower alkyl, lower alkoxy, hydroxy, halo, carboxy, carboalkoxy, amino, amido, sulfonamido and nitrile; a heteroaromatic ring such as substituted- or unsubstituted thiophene, furan, pyrrole, pyridine, or a heteroaromatic ring connected by a lower alkyl chain wherein said heteroaromatic ring is chosen from substituted- or unsubstituted thiophene, furan, pyrrole and pyridine;

$R^5$ is selected from the group consisting of: hydrogen; alkyl; cycloalkyl; alkenyl; alkynyl; phenyl, in which said phenyl group is substituted with hydrogen or from one to three substituent groups each selected from the group consisting of lower alkyl $(C_2-C_6)$, lower alkoxy, hydroxy, halo, carboxy, carboalkoxy, amino, amido, sulfonamido, and nitrile; phenyl lower alkyl in which said phenyl group is substituted with hydrogen or with from one to three substituent groups each selected from the group consisting of lower alkyl, lower alkoxy, hydroxy, halo, carboxy, carboalkoxy, amino, amido, sulfonamido and nitrile;

comprising the steps of (1) reacting a compound of formula (XII) with Merrifield resin to form a compound of formula (XIII):

(XII)

to obtain a compound of formula XIII

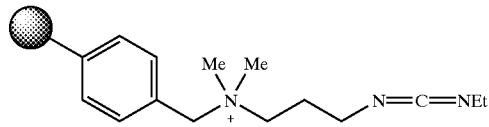
(XIII)

(2) reacting said compound of formula XIII with a compound of formula XIV and an appropriate acid $R^4CO_2H$

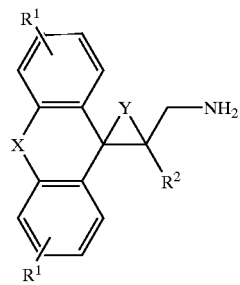
(XIV)

to obtain a compound of formula (1).

33. A method of treating inflammatory conditions comprising applying to the skin of a mammal in need thereof an anti-inflammatory amount of a compound of Formula (I) according to claim 1.

34. A compound according to claim 1, having the name N-(2-carbonyl-5-methylthiophene)-2-(9H-fluoreny-9-yl)-2-phenenylethylamine.

35. A compound according to claim 1, having the name N-(2-propyl) carbonyl-1,2,2-triphenylcydopropylmethylamine.

* * * * *